United States Patent
Budzik et al.

(10) Patent No.: US 8,481,566 B2
(45) Date of Patent: *Jul. 9, 2013

(54) COMPOUNDS WHICH HAVE ACTIVITY AT M1 RECEPTOR AND THEIR USES IN MEDICINE

(75) Inventors: Brian Budzik, Collegeville, PA (US); David Gwyn Cooper, Harlow (GB); Ian Thomson Forbes, Harlow (GB); Vincenzo Garzya, Harlow (GB); Jian Jin, Collegeville, PA (US); Dongchuan Shi, Collegeville, PA (US); Graham Walker, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1403 days.

This patent is subject to a terminal disclaimer.

(21) Appl. No.: 11/852,455

(22) Filed: Sep. 10, 2007

(65) Prior Publication Data

US 2008/0058378 A1 Mar. 6, 2008

Related U.S. Application Data

(63) Continuation of application No. PCT/GB2006/003590, filed on Sep. 27, 2006.

(30) Foreign Application Priority Data

Sep. 30, 2005 (GB) .................................. 0519950.0
Feb. 1, 2006 (GB) .................................. 0602040.8

(51) Int. Cl.
*A61K 31/445* (2006.01)
*C07D 401/04* (2006.01)

(52) U.S. Cl.
USPC .......................................... 514/322; 546/199

(58) Field of Classification Search
USPC .......................................... 514/322; 546/199
See application file for complete search history.

(56) References Cited

U.S. PATENT DOCUMENTS

| | | | |
|---|---|---|---|
| 3,161,645 A | 12/1964 | Adriaan et al. | 546/199 |
| 5,574,044 A | 11/1996 | Thompson et al. | 514/316 |
| 5,691,323 A | 11/1997 | Thompson et al. | 514/94 |
| 5,977,134 A | 11/1999 | Ciccarone et al. | 514/307 |
| 6,162,804 A | 12/2000 | Bilodeau et al. | 514/234.5 |
| 6,465,484 B1 | 10/2002 | Bilodeau et al. | 514/303 |
| 6,872,733 B2 | 3/2005 | Goehring et al. | 514/322 |
| 6,951,849 B2 | 10/2005 | Kelly et al. | 514/210.21 |
| 7,087,593 B2 | 8/2006 | Kelly et al. | 514/183 |
| 7,598,393 B2 | 10/2009 | Kon-I et al. | 548/304.7 |
| 7,776,885 B2 | 8/2010 | Katsu et al. | 514/322 |
| 2002/0019395 A1 | 2/2002 | Zhu et al. | 514/228.2 |
| 2003/0008886 A1 | 1/2003 | Goehring et al. | 514/263.22 |
| 2003/0040513 A1 | 2/2003 | Baxter et al. | 514/224.2 |
| 2003/0100545 A1 | 5/2003 | Kelly et al. | 514/183 |
| 2004/0067931 A1 | 4/2004 | Kelly et al. | 514/210.21 |
| 2005/0002057 A1 | 1/2005 | Cole et al. | 514/217.09 |
| 2005/0192307 A1 | 9/2005 | Goehring et al. | 514/278 |
| 2006/0025402 A1 | 2/2006 | Kelly et al. | 514/210.21 |
| 2006/0199799 A1 | 9/2006 | Kelly et al. | 514/214.03 |
| 2006/0205785 A1 | 9/2006 | Kelly et al. | 514/321 |
| 2006/0258707 A1 | 11/2006 | Kelly et al. | 514/322 |
| 2008/0103178 A1 | 5/2008 | Hashimoto et al. | 514/323 |
| 2008/0293770 A1* | 11/2008 | Budzik et al. | 514/322 |

FOREIGN PATENT DOCUMENTS

| | | |
|---|---|---|
| WO | WO96/13262 | 5/1996 |
| WO | WO2004/089942 | 10/2004 |
| WO | WO2008/119711 | 10/2008 |
| WO | WO2008/119712 | 10/2008 |
| WO | WO2008/119713 | 10/2008 |
| WO | WO2008/119714 | 10/2008 |
| WO | WO 2008/119715 | 10/2008 |
| WO | WO2008/119716 | 10/2008 |
| WO | WO2008/119717 | 10/2008 |
| WO | WO2008/119718 | 10/2008 |
| WO | WO2008/119719 | 10/2008 |
| WO | WO2008/119720 | 10/2008 |
| WO | WO2008/119721 | 10/2008 |

* cited by examiner

*Primary Examiner* — Celia Chang
(74) *Attorney, Agent, or Firm* — Linda E. Hall; John L. Lemanowicz

(57) ABSTRACT

Compounds of formula (I) and salts and solvates are provided:

wherein $R^4$ is fluoro, $R^5$ is selected from hydrogen, halogen, cyano, $C_{1-6}$alkyl, $C_{1-6}$alkyl substituted with one or more fluorine atoms, $C_{1-6}$alkoxy, and $C_{1-6}$alkoxy substituted with one or more fluorine atoms; and $R^6$ is selected from halogen, cyano, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$alkoxy and $C_{1-6}$alkoxy substituted with one or more fluorine atoms, and Q is hydrogen or $C_{1-6}$alkyl. The compounds are expected to be useful for therapy, for example in the treatment of psychotic disorders and cognitive impairment.

7 Claims, No Drawings

COMPOUNDS WHICH HAVE ACTIVITY AT M1 RECEPTOR AND THEIR USES IN MEDICINE

CROSS REFERENCE TO PRIOR APPLICATIONS

This application is a continuation of PCT/GB2006/003590 filed 27 Sep. 2006, which claims priority to GB0519950.0 filed 30 Sep. 2005 and GB0602040.8 filed 1 Feb. 2006.

FIELD OF THE INVENTION

This invention relates to novel compounds, pharmaceutical compositions containing them and their use in therapy, in particular as antipsychotic agents.

BACKGROUND OF THE INVENTION

Muscarinic acetylcholine receptors are members of the G protein coupled receptor superfamily which mediate the actions of the neurotransmitter acetylcholine in both the central and peripheral nervous system. Five muscarinic receptor subtypes have been cloned, $M_1$ to $M_5$. The muscarinic $M_1$ receptor is predominantly expressed in the cerebral cortex and hippocampus, although it is also expressed in the periphery e.g. exocrine glands.

Muscarinic receptors in the central nervous system, especially $M_1$, play a critical role in mediating higher cognitive processing. Diseases associated with cognitive impairments, such as Alzheimer's disease, are accompanied by loss of cholinergic neurons in the basal forebrain. Furthermore, in animal models, blockade or lesion of central cholinergic pathways results in profound cognitive deficits.

Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to side effects resulting from stimulation of peripheral muscarinic receptors including disturbed gastrointestinal motility and nausea.

The dopamine hypothesis of schizophrenia suggests that excess dopaminergic stimulation is responsible for the positive symptoms of the disease, hence the utility of dopamine receptor antagonists to reduce psychotic symptoms. However, conventional dopamine receptor antagonists can cause extrapyramidal side effects (EPS) in patients, including tremor and tardive dyskinesias.

$M_1$ receptor agonists have been sought for the symptomatic treatment of cognitive decline. More recently, a number of groups have shown that muscarinic receptor agonists display an atypical antipsychotic-like profile in a range of pre-clinical paradigms. The muscarinic agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine-induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile.

Xanomeline has also been shown to reduce psychotic symptoms such as suspiciousness, hallucinations and delusions in Alzheimer's patients. However, the relatively non-selective nature of the compound gives rise to dose-limiting peripheral cholinergic side effects.

Selective $M_1$ receptor agonists have the potential utility to ameliorate positive and cognitive symptoms of psychotic disorders such as schizophrenia, schizo-affective disorders, schizophreniform diseases, psychotic depression, mania, acute mania, paranoid and delusional disorders, and cognitive impairment including memory disorders such as Alzheimer's disease without peripheral cholinergic side effects mediated predominantly through $M_2$ and $M_3$ receptors.

$M_1$ receptor agonists may also be suitable for combination with other typical and atypical antipsychotics and other actives such as mood stabilisers, antidepressants, anxiolytics, drugs for extrapyramidal side effects and cognitive enhancers, to provide improved treatment of psychotic disorders.

We have now found a novel group of compounds which are useful for the treatment of psychotic disorders.

SUMMARY OF THE INVENTION

In a first aspect therefore, the invention provides a compound of formula (I) or a salt or solvate thereof:

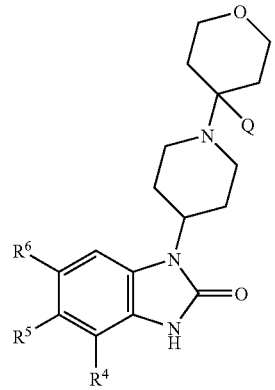

wherein:
$R^4$ is fluoro;
$R^5$ is selected from hydrogen, halogen, cyano, $C_{1-6}$alkyl, $C_{1-6}$alkyl substituted with one or more fluorine atoms, $C_{1-6}$ alkoxy, and $C_{1-6}$ alkoxy substituted with one or more fluorine atoms;
$R^6$ is selected from halogen, cyano, $C_{1-6}$alkyl, $C_{1-6}$alkyl substituted with one or more fluorine atoms, $C_{3-6}$cycloalkyl, $C_{3-6}$cycloalkyl substituted with one or more fluorine atoms, $C_{1-6}$ alkoxy and $C_{1-6}$ alkoxy substituted with one or more fluorine atoms, and
Q is hydrogen or $C_{1-6}$alkyl.

DETAILED DESCRIPTION OF THE INVENTION

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. $C_{1-3}$alkyl means a straight or branched alkyl containing at least 1, and at most 3, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, the term "cycloalkyl" refers to a non-aromatic hydrocarbon ring containing the specified number of carbon atoms. For example, $C_{3-6}$cycloalkyl means a non-aromatic ring containing at least three, and at most six, ring carbon atoms. Examples of "cycloalkyl" as used herein include, but are not limited to, cyclopropyl, cyclobutyl, cyclopentyl and cyclohexyl.

As used herein, the term "halogen" (or the abbreviated form "halo") refers to the elements fluorine (which may be abbreviated to "fluoro"), chlorine (which may be abbreviated to "chloro"), bromine (which may be abbreviated to "bromo") and iodine (which may be abbreviated to "iodo"). Examples of halogens are fluorine, chlorine and bromine.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. If the solvent used is water, the solvate may be referred to as a hydrate.

As used herein, the term "substituted" refers to substitution with the named substituent or substituents, multiple degrees of substitution being allowed unless otherwise stated. For example, there may be 1, 2, 3 or 4 substituents on a given substituted group. For example, if $R^6$ is a $C_{1-6}$alkyl group, it may be substituted by 1, 2, 3 or 4 fluoro groups; and if $R^6$ is a $C_{1-6}$alkoxy group, it may be substituted by 1, 2, 3 or 4 fluoro groups. For example, $R^6$ may be a $C_{1-6}$alkyl group substituted by 3 fluoro groups; and $R^6$ may be a $C_{1-6}$alkoxy group substituted by 3 fluoro groups.

In one embodiment, $R^5$ is selected from hydrogen, halogen, cyano, $C_{1-6}$alkyl, $C_{1-6}$alkyl substituted with one, two or three fluorine atoms, $C_{1-6}$ alkoxy, and $C_{1-6}$ alkoxy substituted with one, two or three fluorine atoms.

In one embodiment, $R^5$ is selected from hydrogen, chloro, bromo, fluoro, $C_{1-4}$alkyl, $C_{1-4}$alkyl substituted with one or more fluorine atoms, and $C_{1-4}$alkoxy.

In one embodiment, $R^5$ is selected from hydrogen, chloro, bromo, fluoro, $C_{1-4}$alkyl, $C_{1-4}$alkyl substituted with one, two or three fluorine atoms, and $C_{1-4}$alkoxy.

In one embodiment, $R^5$ is selected from hydrogen, chloro, bromo, fluoro, methyl, ethyl, methoxy and trifluoromethyl.

In one embodiment, $R^5$ is hydrogen or fluoro.

In one embodiment, $R^6$ is selected from halogen, cyano, $C_{1-6}$alkyl, $C_{1-6}$alkyl substituted with one, two or three fluorine atoms, $C_{3-6}$cycloalkyl, $C_{3-6}$cycloalkyl substituted with one, two or three fluorine atoms, $C_{1-6}$ alkoxy and $C_{1-6}$ alkoxy substituted with one, two or three fluorine atoms.

In one embodiment of the invention, $R^6$ is selected from halogen, $C_{1-6}$alkyl, $C_{1-6}$ alkyl substituted with one or more fluorine atoms, $C_{3-6}$cycloalkyl, $C_{3-6}$cycloalkyl substituted with one or more fluorine atoms, $C_{1-6}$ alkoxy and $C_{1-6}$ alkoxy substituted with one or more fluorine atoms.

In another embodiment of the invention, $R^6$ is selected from chloro, bromo, fluoro, methyl, ethyl, isopropyl, methoxy, trifluoromethoxy and trifluoromethyl, for example chloro, fluoro, methyl, methoxy, trifluoromethoxy and trifluoromethyl.

In a further embodiment of the invention, $R^6$ is selected from chloro, methyl and methoxy.

In one embodiment, $R^6$ is selected from chloro, bromo, fluoro, methyl, ethyl, isopropyl, cyclopropyl, methoxy, trifluoromethoxy and trifluoromethyl.

In another embodiment, $R^6$ is chloro, fluoro, methyl, cyclopropyl, methoxy, trifluoromethoxy or trifluoromethyl.

In one embodiment, $R^6$ is selected from methyl, fluoro, chloro, methoxy and cyclopropyl.

In one embodiment of the invention, Q is selected from hydrogen and $C_{1-3}$alkyl. In a further embodiment, Q is selected from hydrogen, methyl, ethyl and propyl. In one embodiment, Q is hydrogen or methyl. In one embodiment, Q is hydrogen.

In another embodiment of the invention, there is provided a compound of formula (Ia):

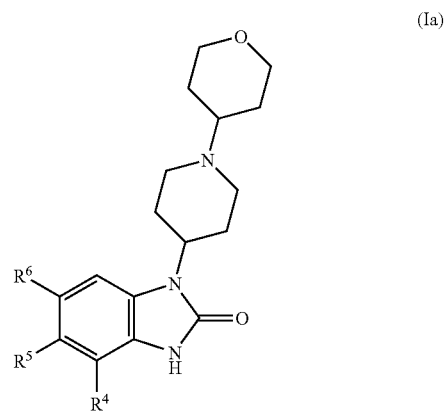

(Ia)

wherein:
$R^4$ is fluoro;
$R^5$ is selected from hydrogen, halogen, $C_{1-6}$alkyl, $C_{1-6}$alkyl substituted with one or more fluorine atoms, $C_{1-6}$ alkoxy, and $C_{1-6}$ alkoxy substituted with one or more fluorine atoms; and
$R^6$ is selected from halogen, $C_{1-6}$alkyl, $C_{1-6}$ alkyl substituted with one or more fluorine atoms, $C_{3-6}$cycloalkyl, $C_{3-6}$cycloalkyl substituted with one or more fluorine atoms, $C_{1-6}$ alkoxy and $C_{1-6}$ alkoxy substituted with one or more fluorine atoms,
or a pharmaceutically acceptable salt or solvate thereof.

In another embodiment, the invention provides a compound of formula (Ib):

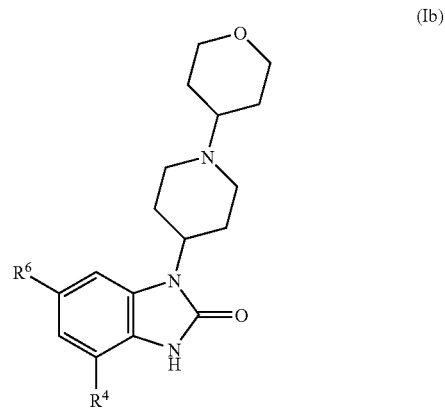

(Ib)

wherein:

$R^4$ is fluoro; and $R^6$ is selected from hydrogen, halogen, $C_{1-6}$alkyl, $C_{1-6}$ alkyl substituted with one or more fluorine atoms, $C_{3-6}$cycloalkyl, $C_{3-6}$cycloalkyl substituted with one or more fluorine atoms, $C_{1-6}$ alkoxy and $C_{1-6}$ alkoxy substituted with one or more fluorine atoms, or a pharmaceutically acceptable salt or solvate thereof.

All features and embodiments for formula (I) apply to compounds of formula (Ia) and (Ib) mutatis mutandis. Hereinafter, all references to compounds of formula (I) include compounds of formula (Ia) and compounds of formula (Ib).

It will be appreciated that for use in medicine the salts of formula (I) should be pharmaceutically acceptable. Suitable salts will be apparent to those skilled in the art and include for example acid salts, for example sodium, potassium, calcium, magnesium and tetraalkylammonium and the like, or mono- or di-basic salts formed with inorganic acids e.g. hydrochloric, hydrobromic, sulfuric, nitric or sulfamic phosphoric acid; and organic acids e.g. succinic, maleic, malic, mandelic, acetic, isethionic fumaric, glutamic, lactic, citric, tartaric, benzoic, lactobionic benzenesulfonic, p-toluenesulfonic, methanesulfonic ethanesulfonic or naphthalenesulfonic acid. Examples of salts further include trifluoroacetate salts and formate salts. Other non-pharmaceutically acceptable salts e.g. oxalates, may be used, for example in the isolation of compounds of formula (I) and are included within the scope of this invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain of the compounds of formula (I) may form acid addition salts with less than one (for example, 0.5 equivalent of a dibasic acid) or one or more equivalents of an acid. The present invention includes within its scope all possible stoichiometric and non-stoichiometric forms thereof.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

The present invention includes within the scope all pharmaceutically acceptable derivatives of the compounds of formula (I). As used herein, the term "pharmaceutically acceptable derivative", means any pharmaceutically acceptable salt, solvate, or prodrug e.g. ester, of a compound of formula (I), which upon administration to the recipient is capable of providing (directly or indirectly) a compound of formula (I), or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. Examples of suitable protecting groups for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Suitable prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Particular compounds according to the invention include those specifically exemplified in the Examples section and named hereinafter including, without limitation:—
4-Fluoro-6-methyl-1-[1-(tetrahydro-2H-pyran-4-yl)-4-piperidinyl]-1,3-dihydro-2H-benzimidazol-2-one
6-Chloro-4-fluoro-1-[1-(tetrahydro-2H-pyran-4-yl)-4-piperidinyl]-1,3-dihydro-2H-benzimidazol-2-one
4-Fluoro-6-methoxy-1-[1-(tetrahydro-2H-pyran-4-yl)-4-piperidinyl]-1,3-dihydro-2H-benzimidazol-2-one
4,5-Difluoro-6-methyl-1-[1-(tetrahydro-2H-pyran-4-yl)-4-piperidinyl]-1,3-dihydro-2H-benzimidazol-2-one
6-Cyclopropyl-4-fluoro-1-[1-(tetrahydro-2H-pyran-4-yl)-4-piperidinyl]-1,3-dihydro-2H-benzimidazol-2-one
4,5-Difluoro-6-methyl-1-[1-(4-methyltetrahydro-2H-pyran-4-yl)-4-piperidinyl]-1,3-dihydro-2H-benzimidazol-2-one
and salts and solvates thereof, for example the hydrochloride salt, the trifluoroacetate salt or the formate salt of any of the above compounds.

Specific examples of salts of the present invention include:
4-Fluoro-6-methyl-1-[1-(tetrahydro-2H-pyran-4-yl)-4-piperidinyl]-1,3-dihydro-2H-benzimidazol-2-one hydrochloride
4-Fluoro-6-methyl-1-[1-(tetrahydro-2H-pyran-4-yl)-4-piperidinyl]-1,3-dihydro-2H-benzimidazol-2-one monocitrate
4-Fluoro-6-methyl-1-[1-(tetrahydro-2H-pyran-4-yl)-4-piperidinyl]-1,3-dihydro-2H-benzimidazol-2-one methanesulfonate
6-Chloro-4-fluoro-1-[1-(tetrahydro-2H-pyran-4-yl)-4-piperidinyl]-1,3-dihydro-2H-benzimidazol-2-one hydrochloride
4-Fluoro-6-methoxy-1-[1-(tetrahydro-2H-pyran-4-yl)-4-piperidinyl]-1,3-dihydro-2H-benzimidazol-2-one hydrochloride
4,5-Difluoro-6-methyl-1-[1-(tetrahydro-2H-pyran-4-yl)-4-piperidinyl]-1,3-dihydro-2H-benzimidazol-2-one hydrochloride 6-Cyclopropyl-4-fluoro-1-[1-(tetrahydro-2H-pyran-4-yl)-4-piperidinyl]-1,3-dihydro-2H-benzimidazol-2-one hydrochloride and 4,5-Difluoro-6-methyl-1-[1-(4-methyltetrahydro-2H-pyran-4-yl)-4-piperidinyl]-1,3-dihydro-2H-benzimidazol-2-one hydrochloride.

In a further embodiment, the invention provides a general process (A1) for preparing compounds of formula (I), in which Q=H, which process comprises:

coupling a compound of formula (II)

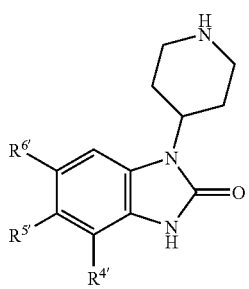

(II)

with a compound of formula (III)

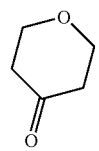

(III)

wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$.

The reaction is carried out under conditions suitable for reductive alkylation. The reductive alkylation reaction is typically carried out using sodium triacetoxyborohydride in dichloroethane, optionally in the presence of triethylamine, and optionally in the presence of titanium tetraisopropoxide. Alternatively sodium cyanoborohydride can be used as the reducing reagent in solvents such as methanol or ethanol, or the reductive alkylation can be effected under catalytic hydrogenation conditions using a palladium catalyst. In a further variation, the compounds (II) and (III) can be condensed under dehydrating conditions e.g. molecular sieves or magnesium sulfate, and the resultant imine or enamine reduced using for example sodium borohydride or by catalytic hydrogenation.

A modification of general process (A1) is required where $Q=C_{1-6}$ alkyl. Thus, in general process (A2), a compound of formula (II) can be reacted with a compound of formula (III) in the presence of a source of cyanide, e.g. potassium cyanide or acetone cyanohydrin, to form the cyano intermediate (XXXX) which can be reacted with an alkyl Grignard reagent QMgX to form compounds of formula (I).

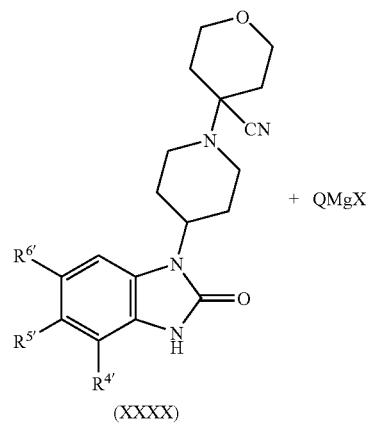

+ QMgX (XXXX)

wherein $R^{5'}$ is a group $R^5$ as previously defined, or a group convertible to $R^5$, $R^{6'}$ is a group $R^6$ as previously defined, or a group convertible to $R^6$, $R^{4'}$ is a group R4 as previously defined, or a group convertible to R4, Q is hydrogen or $C_{1-6}$alkyl, and X is chloro, bromo or iodo.

The reaction is carried out using conditions similar to those described in the literature (Arch Pharm (Weinheim), 1987, 320 (4), 348-361). The piperidine and ketone components are treated with potassium cyanide in water at pH3 or reacted with acetone cyanohydrin in dimethylacetamide at elevated temperature to form the adduct (XXXX). Reaction of the adduct (XXXX) with the alkyl Grignard reagent QMgX in ether or tetrahydrofuran provides compounds of formula (I).

In a further embodiment, the invention provides a general process (B) for preparing compounds of formula (I) which process comprises:

coupling a compound of formula (IV)

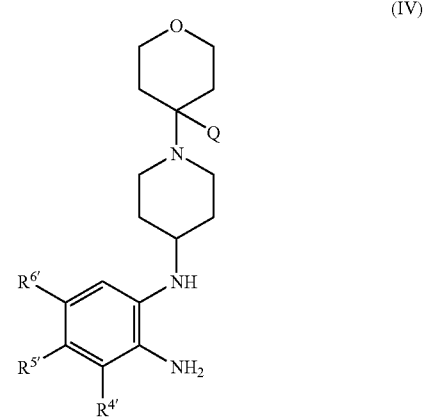

(IV)

with a compound of formula (V)

(V)

wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, Q is hydrogen or $C_{1-6}$alkyl, and X and Y both represent leaving groups. X and Y can be the same or different and examples are Cl, PhO, EtO, imidazole. When X and Y are both Cl, i.e. phosgene, this reagent can be generated in situ e.g. from diphosgene or triphosgene.

The above reaction is carried out using standard methodology e.g. reacting the diamine (IV) with the reagent (V) in an inert solvent for example dichloromethane or toluene or dimethylformamide, optionally in the presence of a base such as triethylamine or potassium carbonate, and optionally with heating.

In a further embodiment, the invention provides a general process (C) for preparing compounds of formula (I) which process comprises:

treatment of a compound of formula (VI)

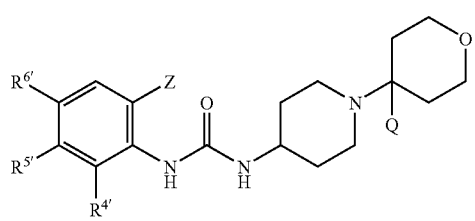

(VI)

with a palladium or copper catalyst (VII) to effect an intramolecular cyclisation wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, Q is hydrogen or $C_{1-6}$alkyl, and Z is a leaving group such as bromo, iodo, chloro or triflate.

The cyclisation reaction can be carried out using a variety of palladium or copper reagents as described in the literature (JACS, 2003, 125, 6653, Tet. Lett., 2004, 45, 8535, or JACS, 2002, 124, 7421.)

In a further embodiment, the invention provides a general process (D) for preparing compounds of formula (I) which process comprises:

coupling a compound of formula (VIII)

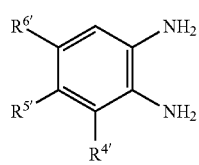

(VIII)

with a compound of formula (IX)

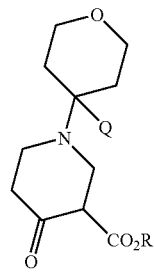

(IX)

wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, Q is hydrogen or $C_{1-6}$alkyl, and R is a $C_{1-5}$alkyl group.

This condensation and cyclisation reaction can be carried out under reaction conditions similar to those described in the literature for an analogous process (U.S. Pat. No. 3,161,645) (e.g. heating in an inert solvent such as xylene) followed by reduction of the piperidine double bond using for example catalytic hydrogenation over palladium or Raney nickel.

In a further embodiment, the invention provides a general process (E) for preparing compounds of formula (I) which process comprises:

reaction of a compound of formula (X)

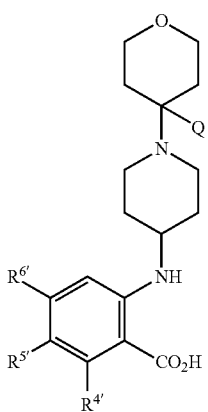

(X)

with diphenylphosphoryl azide or other reagent/combination of reagents to effect the Curtius rearrangement of compound (X), followed by intramolecular cyclisation.

wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, and Q is hydrogen or $C_{1-6}$alkyl.

The Curtius rearrangement is typically carried out by mixing the two reactants in an inert solvent such as toluene, optionally with heating.

In a further aspect, the invention provides a general process (F) for preparing compounds of formula (I) which process comprises:
coupling a compound of formula (XI)

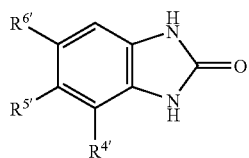

(XI)

with a compound of formula (XII)

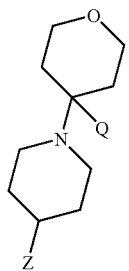

(XII)

wherein $R^{4'}$ is a Group $R^4$ as Previously Defined, or a Group Convertible to $R^4$, $R^{5'}$ is a Group $R^5$ as previously defined, or a group convertible to $R^5$, and $R^{6'}$ is a group $R^6$ as previously defined, or a group convertible to $R^6$, Q is hydrogen or $C_{1-6}$alkyl, and Z is hydroxy or a leaving group such as chloro, bromo or iodo, or alkyl/aryl sulfonate.

The alkylation reaction (Z=a leaving group) can be carried out under classical alkylation or Mitsunobu reaction (Z=OH) conditions. Using classical alkylation conditions, the benzimidazolone intermediate (XI) can be deprotonated using a base such as sodium hydride in an inert solvent such as dimethylformamide, and then treated with the alkylating reagent (XII), optionally with heating. The Mitsunobu reaction with (XII) Z=OH can be carried out using standard conditions e.g. triphenylphosphine and diethylazodicarboxylate in an inert solvent such as dichloromethane or tetrahydrofuran at room temperature Conversion of $R^{6'}$ to $R^6$ or interconversions of $R^6$ may be accomplished as indicated below.

For example, when $R^{6'}$ is a halogen, it can be converted to an alkoxy or trifluoromethyl group by copper catalysed reaction, using an alcohol, or methyl fluorosulfonyl(difluoro)acetate, respectively. It may also be converted to an alkyl group with an organometallic reagent, for example an alkylstannane.

As another example, when $R^{6'}$ is hydroxy, it may be converted to alkoxy by reaction with an alkyl halide or sulfonate, or to trifluoromethoxy by conversion to the xanthate followed by oxidation in the presence of fluoride ion.

As a further example, when $R^{6'}$ is methyl, it may be converted to trifluoromethyl by chlorination or bromination followed by displacement of the introduced halogens with fluoride.

Conversion of $R^{5'}$ to $R^5$ or interconversions or $R^5$ may be accomplished in a manner similar to that indicated for conversion of $R^{6'}$ to $R^6$ or interconversions or $R^6$.

Conversion of R4' to R4 may be accomplished in various ways; for example by displacement of a halide group by fluoride, or by fluorination of an organometallic derivative with a source of electrophilic fluorine such as N-fluorobenzenesulfonimide, or by decomposition of a diazonium tetrafluoroborate.

Compounds of formula (II) are generally known in the literature or can be prepared by a range of different processes for example:

(a) displacement of an ortho-fluoro or ortho-chloro nitrobenzene intermediate (XIII) with the amine (XIV), wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, and P represents a nitrogen protecting group e.g. Boc, acetyl, trifluoroacetyl, ethoxycarbonyl, benzyloxycarbonyl, to give (XXIII), followed by reduction of the nitro group, cyclisation using phosgene or a phosgene equivalent, and deprotection of the piperidine nitrogen using standard literature conditions (Scheme 1).

Scheme 1

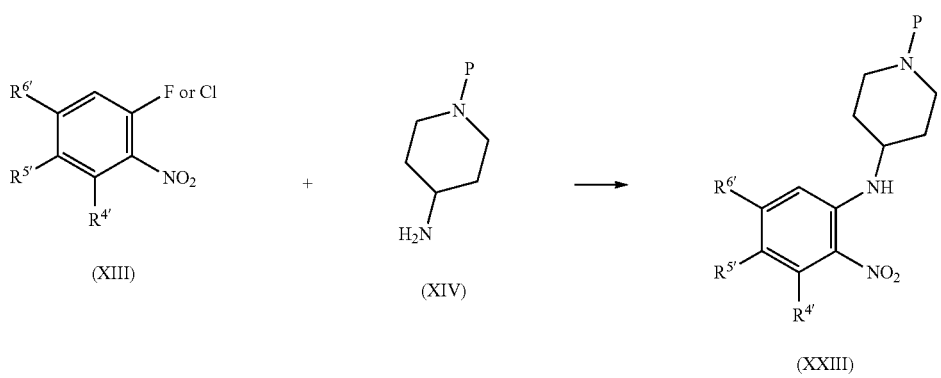

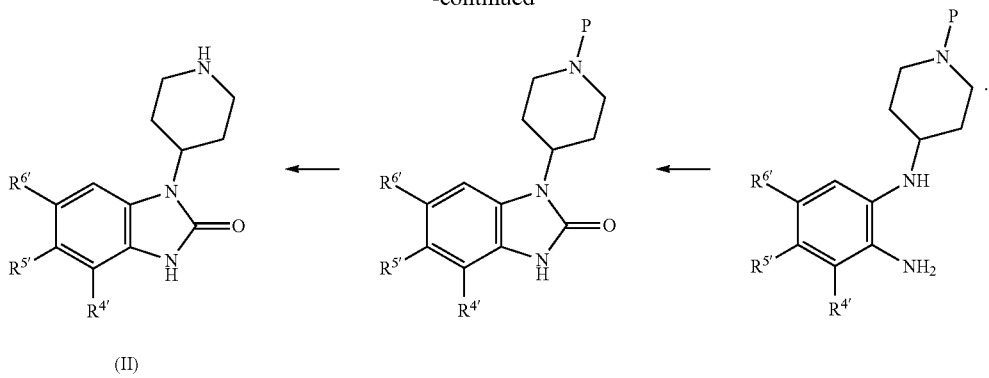

(II)

Compounds of formula (XIII) are commercially available or can be prepared by standard methodology. The compound (XIV) in which P=Boc is commercially available (b) metal catalysed cyclisation of an intermediate (XV) followed by deprotection of the piperidine nitrogen, wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, P represents a nitrogen protecting group e.g. Boc, acetyl, trifluoroacetyl, benzyloxycarbonyl, and Z represents a leaving group such as bromo, iodo, chloro or triflate. Reaction conditions for the Buchwald cyclisation are summarised in Process C. The urea (XV) can be prepared using any of the classical methods for urea formation as illustrated in Scheme 2. The starting materials for this process are commercially available or can be prepared using standard methodology.

Scheme 2.

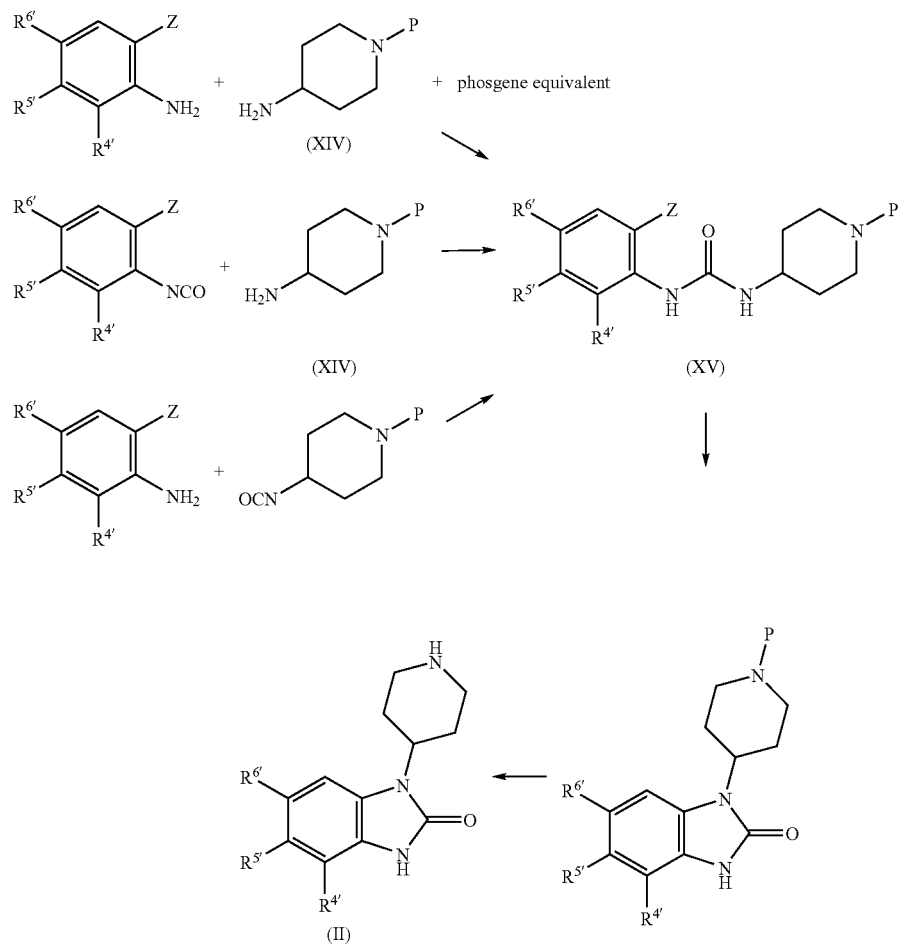

(c) Curtius rearrangement of an intermediate (XVI), wherein $R^{4'}$ is a group $R^4$ as previously defined, or a group convertible to $R^4$, $R^{5'}$ is a group $R^{5'}$ as previously defined, or a group convertible to $R^5$, and $R^{6'}$ is a group $R^6$ as previously defined, or a group convertible to $R^6$, P represents a nitrogen protecting group e.g. Boc, acetyl, trifluoroacetyl, benzyloxycarbonyl, and R represents H or a C1-5 alkyl group e.g. methyl or ethyl, followed by intramolecular cyclisation and deprotection of the piperidine nitrogen (Scheme 3). The anthranilic acid or ester starting materials (XVII) are commercially available or can be made by standard methodology. The piperidone starting material (R=Boc or benzyl) is commercially available. The Curtius rearrangement can be effected using the conditions described under process E.

(d) Condensation of an orthophenylenediamine (VIII) with a 3-alkoxycarbonyl-4-piperidone (XX), wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, P represents a nitrogen protecting group e.g. Boc, acetyl, trifluoroacetyl, benzyloxycarbonyl and R is a C1-5 alkyl group (Scheme 4.), by heating in an inert solvent at elevated temperature, to afford the tetrahydropyridine intermediate (XXI). Hydrogenation of the double bond and deprotection of the piperidine nitrogen can be accomplished separately or concomitantly dependent on the precise nature of the protecting group P, to afford the desired product (II). Compounds of formula (VIII) are commercially available or can be prepared by standard methodology. Compounds of formula (XX) are commercially available or can be prepared by standard methodology.

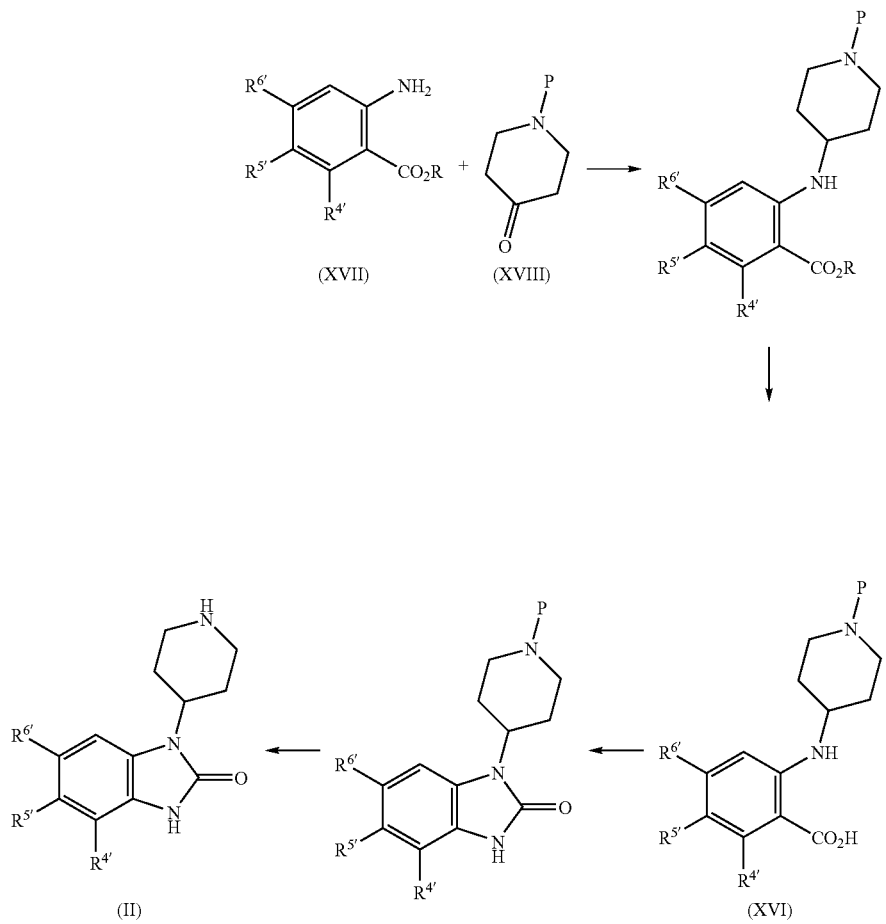

Scheme 3.

Scheme 4.

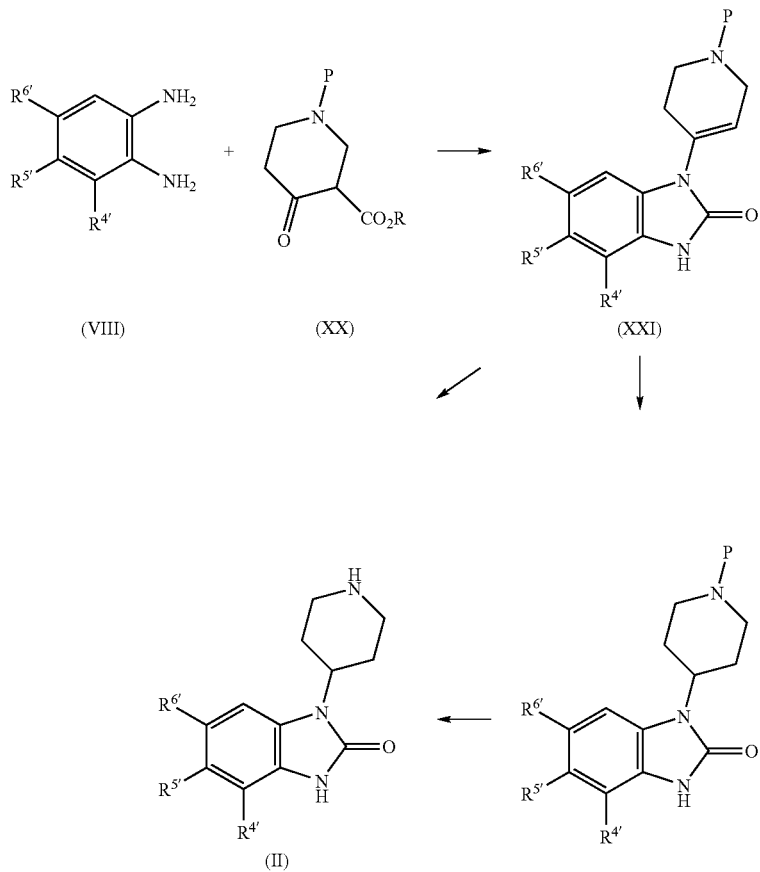

(e) Reductive alkylation of an ortho nitroaniline (XXII) with an N-protected 4-piperidone (XVIII), wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, and P represents a nitrogen protecting group e.g. Boc, acetyl, trifluoroacetyl, benzyloxycarbonyl, using for example sodium triacetoxyborohydride to give the intermediate (XXIII). Reduction of the nitro group, followed by cyclisation and deprotection as described hereinbefore provides the desired product (II) (Scheme 5). Compounds of formula (XXII) and (XVIII) are commercially available or can be prepared by standard methodology Scheme 5.

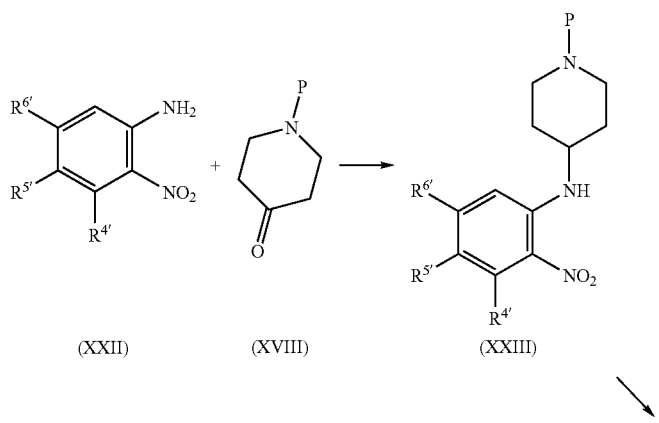

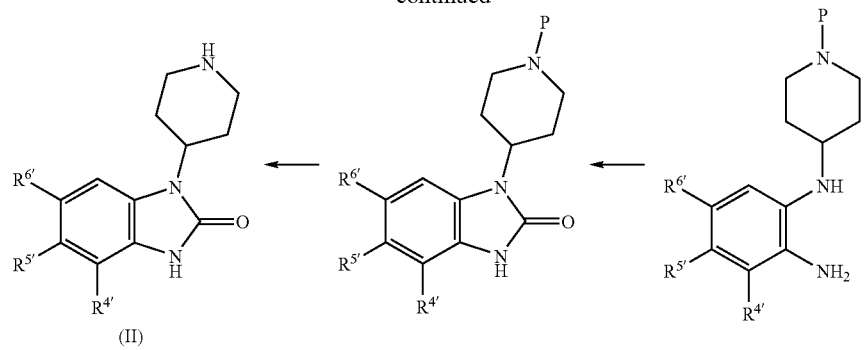

(f) metal catalysed reaction between the amine (XIV) and a suitably substituted nitrobenzene compound (XXIV) wherein R⁴' is a group R⁴ as previously defined, or a group convertible to R⁴, R⁵' is a group R⁵ as previously defined, or a group convertible to R⁵, and R⁶' is a group R⁶ as previously defined, or a group convertible to R⁶, P represents a nitrogen protecting group e.g. Boc, acetyl, trifluoroacetyl, benzyloxycarbonyl, and Z represents a leaving group such as bromo, iodo, chloro or triflate (Scheme 6). This process generates intermediates of formula (XXIII) and subsequent reactions are similar to that for Scheme 5. Compounds of formula (XXIV) are commercially available or can be prepared by known methodology. The compound (XIV) in which P=Boc is commercially available.

(g) metal catalysed reaction between the amine (XIV) and the protected aniline (XXV), wherein R⁴' is a group R⁴ as previously defined, or a group convertible to R⁴, R⁵' is a group R⁵ as previously defined, or a group convertible to R⁵, and R⁶' is a group R⁶ as previously defined, or a group convertible to R⁶, P represents a nitrogen protecting group e.g. Boc, acetyl, trifluoroacetyl, benzyloxycarbonyl, and Z represents a leaving group such as bromo, iodo, chloro or triflate, to give the intermediate (XXVI) (Scheme 7). Deprotection of the aniline followed by the same reaction sequence as in Scheme 6 affords the desired intermediate (II). Compounds of formula (XXV) are commercially available or can be prepared by known methodology e.g. halogenation ortho to the aniline group. The compound (XIV) in which P=Boc is commercially available Scheme 6.

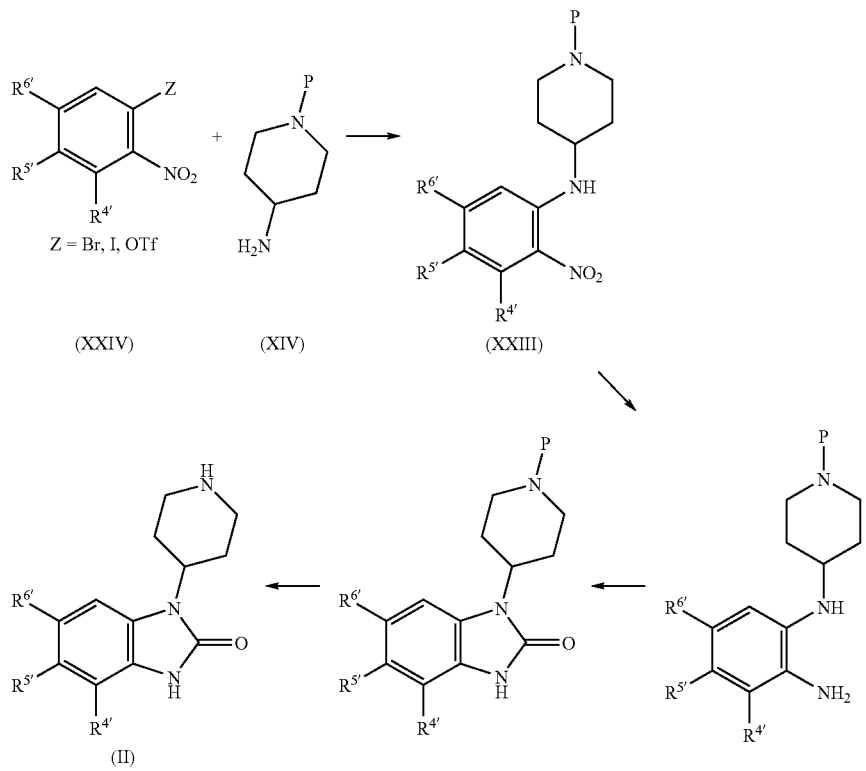

Scheme 7.

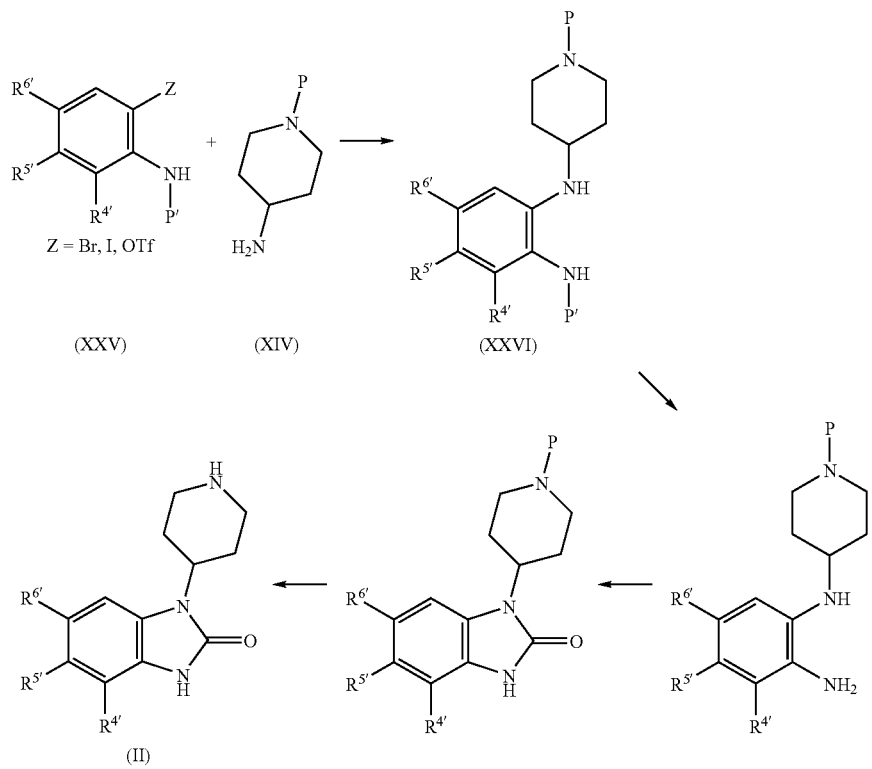

The compound of formula (III) is commercially available.

Compounds of formula (IV) can be prepared by a number of different processes e.g.

(h) displacement of an ortho-fluoro or ortho-chloro nitrobenzene intermediate (XIII) with the amine (XXVII) to afford compound (XXVIII) wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, and Q is hydrogen or $C_{1-6}$alkyl, followed by reduction of the nitro group using standard conditions e.g. hydrogenation over palladium or Raney nickel (Scheme 8). Compounds of formula (XIII) are commercially available or can be prepared by standard methodology.

Scheme 8.

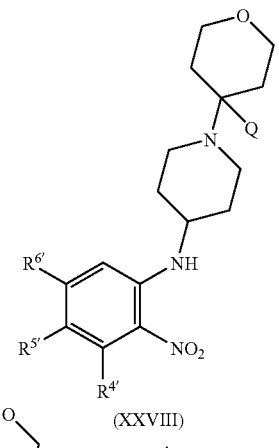

-continued

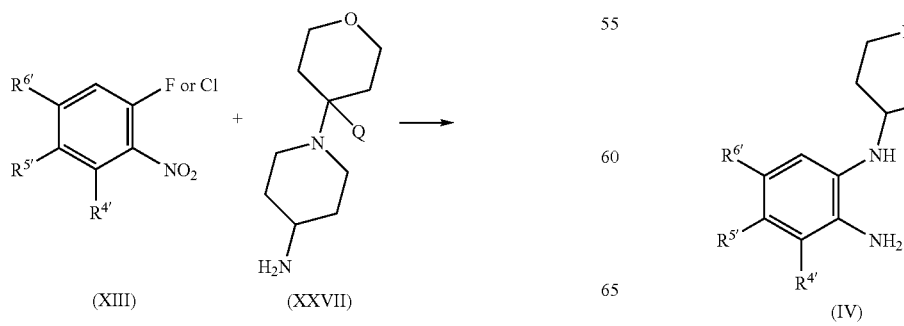

(i) metal catalysed reaction of the amine (XXVII) with the ortho substituted nitrobenzene (XXIX) to afford compound (XXVIII) wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$ (Scheme 9) and Q is hydrogen or $C_{1-6}$alkyl, followed by the same reactions as illustrated in Scheme 8. Compounds of formula (XXIX) are commercially available or can be prepared by standard methodology.

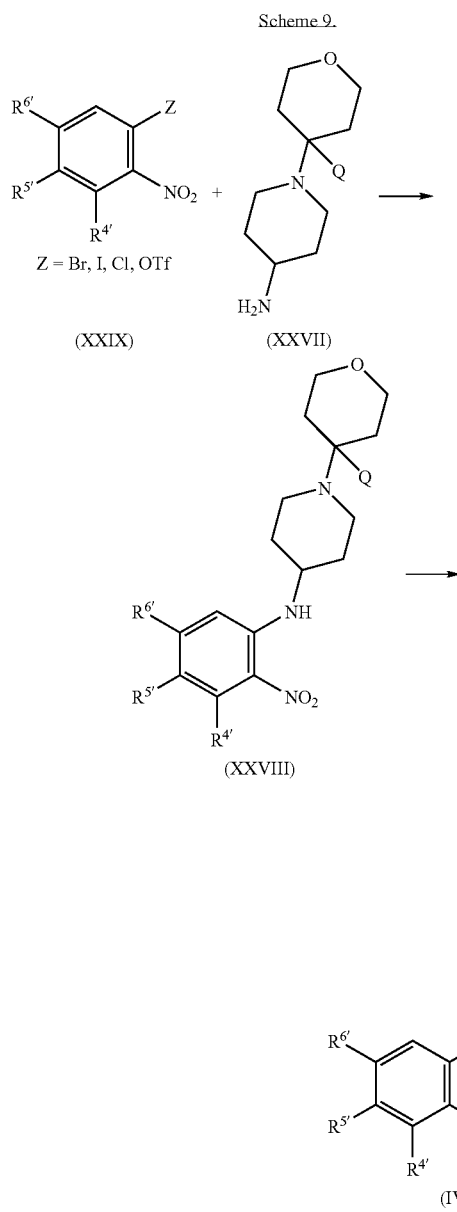

(j) metal catalysed reaction of the amine (XXVII) with the protected aniline derivative (XXV), wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, Q is hydrogen or $C_{1-6}$alkyl, and P represents a nitrogen protecting group such as acetyl, trifluoroacetyl, Boc, phthalimide, to afford compound (XXXI) (Scheme 10) followed by deprotection of the aniline group. Compounds of formula (XXV) are commercially available or can be prepared by standard methodology.

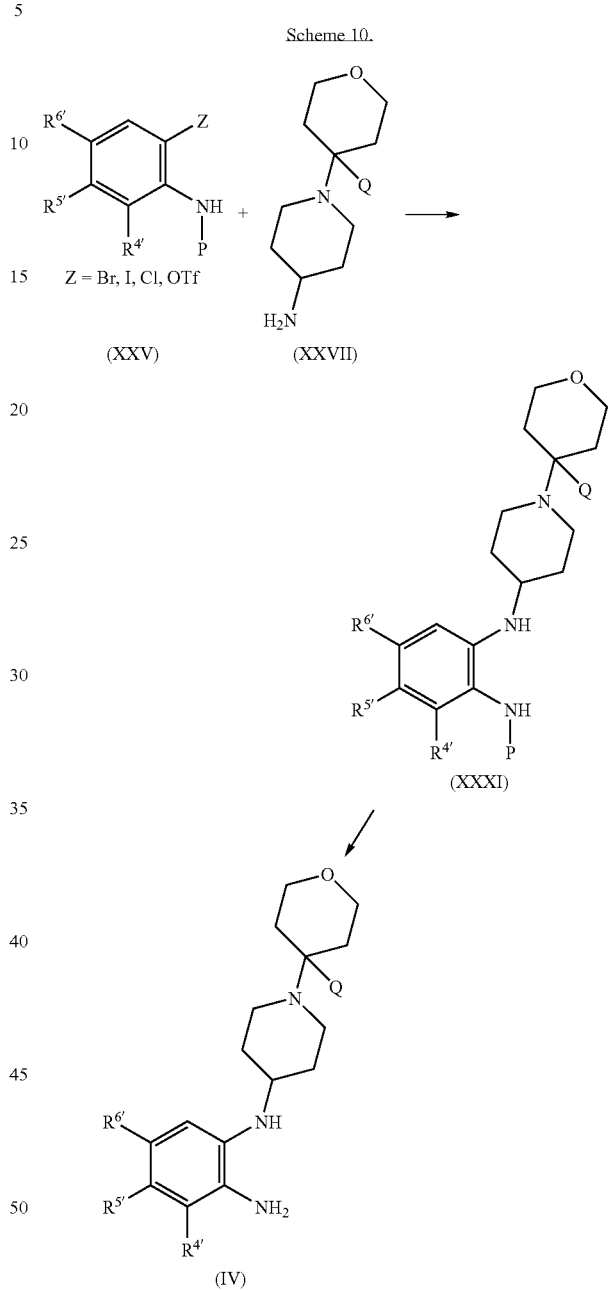

(k) Reductive alkylation of an ortho nitroaniline (XXII) with the piperidone (XXXII) using for example sodium triacetoxyborohydride in dichloroethane to give the intermediate (XXVIII) wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, and Q is hydrogen or $C_{1-6}$alkyl, using for example sodium triacetoxyborohydride in dichloroethane to give the intermediate (XXVIII) (Scheme 11). Reduction of the nitro group using, for example, palladium on carbon or Raney nickel affords the desired intermediate (IV).

Scheme 11.

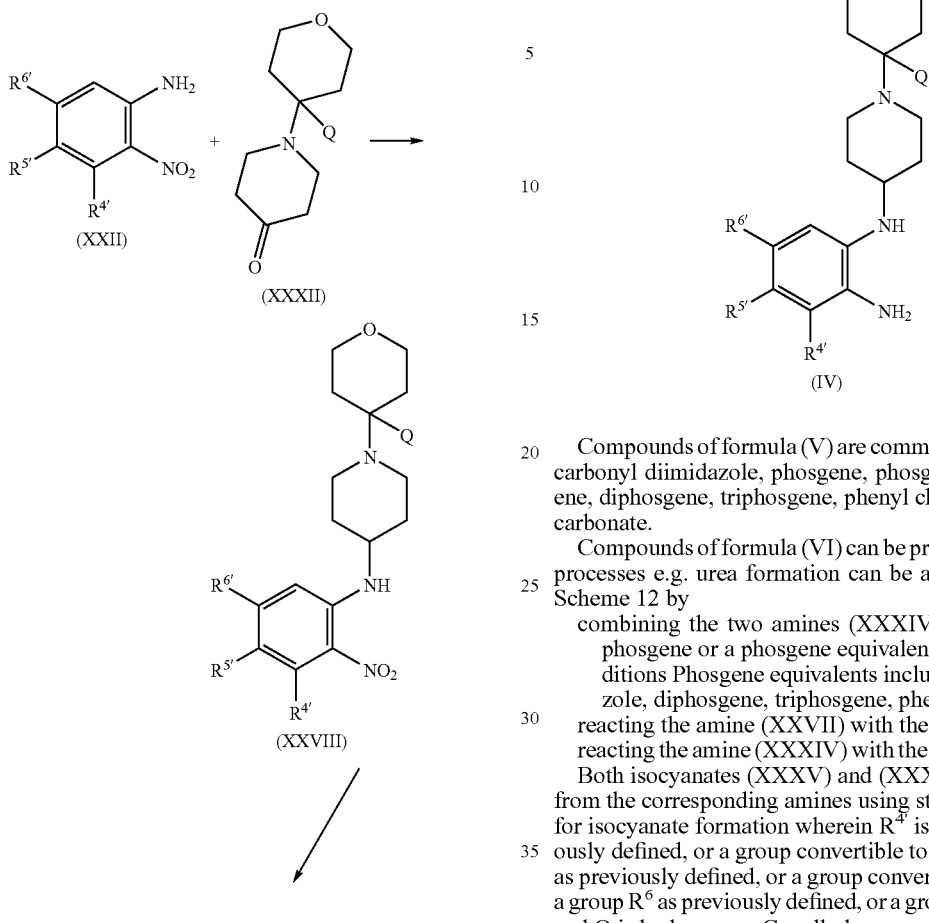

Compounds of formula (V) are commercially available e.g. carbonyl diimidazole, phosgene, phosgene solution in toluene, diphosgene, triphosgene, phenyl chloroformate, diethyl carbonate.

Compounds of formula (VI) can be prepared by a variety of processes e.g. urea formation can be achieved as shown in Scheme 12 by
- combining the two amines (XXXIV) and (XXVII) with phosgene or a phosgene equivalent using standard conditions Phosgene equivalents include carbonyl diimidazole, diphosgene, triphosgene, phenyl chloroformate
- reacting the amine (XXVII) with the isocyanate (XXXV)
- reacting the amine (XXXIV) with the isocyanate (XXXVI)

Both isocyanates (XXXV) and (XXXVI) can be prepared from the corresponding amines using standard methodology for isocyanate formation wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, and Q is hydrogen or $C_{1-6}$alkyl.

Scheme 12.

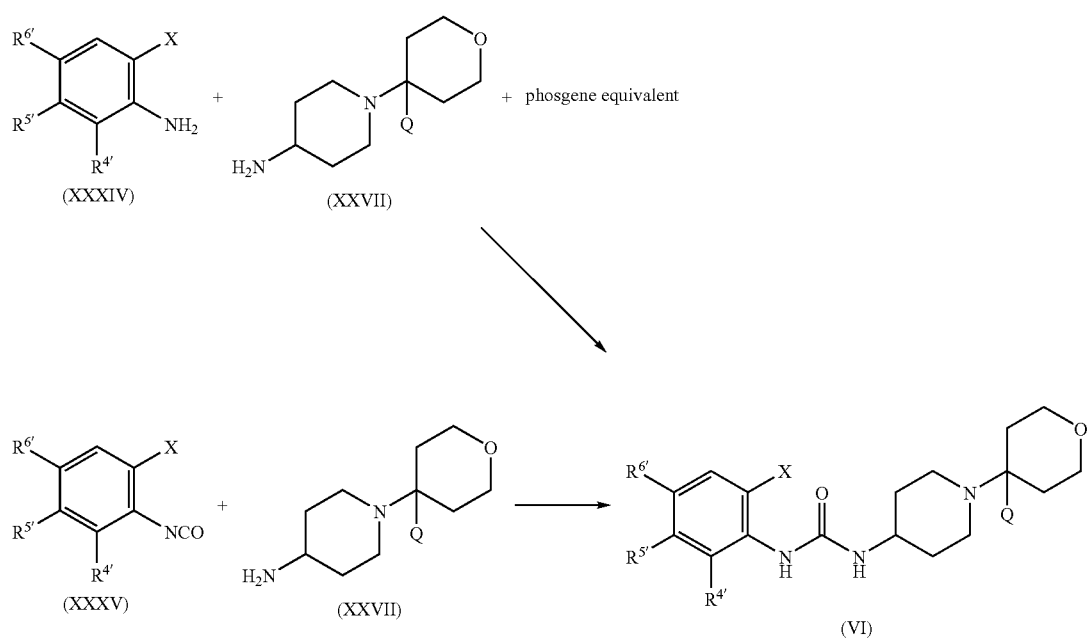

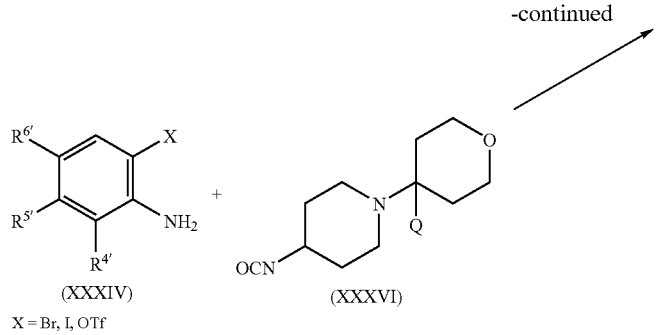

(XXXIV)  (XXXVI)

X = Br, I, OTf

Palladium and copper catalysts (VII) are commercially available or can be prepared as described in the literature (see references in Process C).

Compounds of formula (VIII) are commercially available or can be prepared by known literature routes e.g. reduction of a mono or dinitrobenzene precursor.

Compounds of formula (IX) can be prepared by reductive alkylation of the 3-alkoxycarbonyl-4-piperidone with tetrohydropyran-4-one.

Compounds of formula (X) wherein $R^{4'}$ is a group $R^4$ as previously defined, or a group convertible to $R^4$, $R^{5'}$ is a group $R^5$ as previously defined, or a group convertible to $R^5$, and $R^{6'}$ is a group $R^6$ as previously defined, or a group convertible to $R^6$, and Q is hydrogen or $C_{1-6}$alkyl, can be prepared as shown in Scheme 13. Reductive alkylation of an anthranilic acid or ester (XVII) with the ketone (XXXII), followed if appropriate by hydrolysis of the ester group.

Scheme 13.

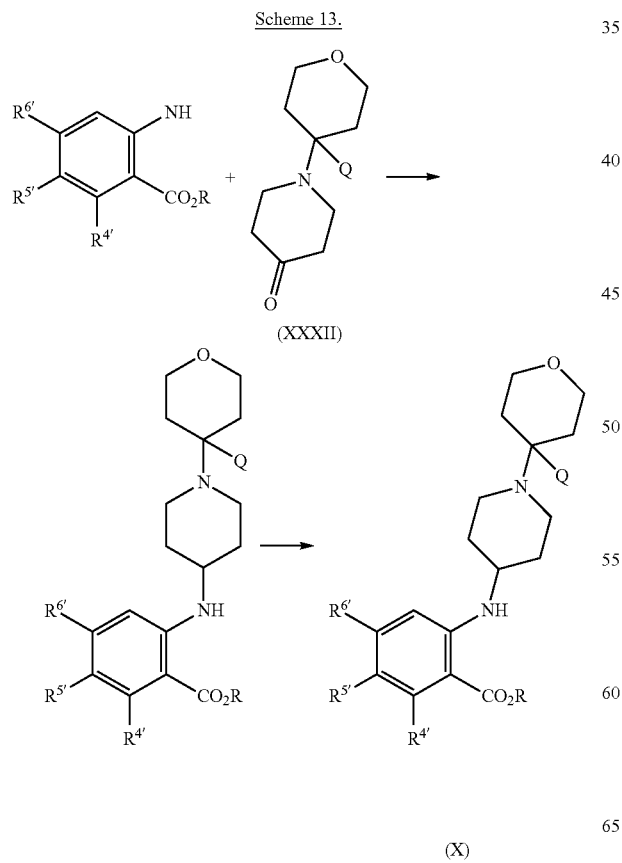

Compounds of formula (XI) are commercially available or can be prepared by literature processes.

Compounds of formula (XII) can be prepared as shown in Scheme 14, by reductive alkylation of (XXXVII) where Z' represents Z or a group convertible to Z with the ketone (III), and Q=H. Conversion of a Z' hydroxy group to Z=chloro or bromo can be accomplished using standard methodology e.g. treatment with thionyl chloride or triphenylphosphine/carbon tetrabromide.

Scheme 14.

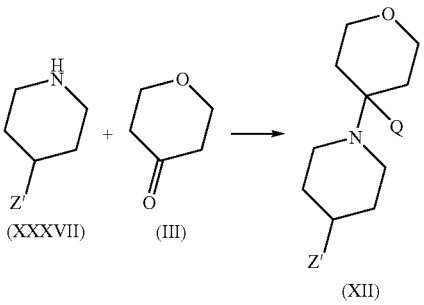

(XXXVII)  (III)

(XII)

The Compound (XXVII) where Q=H can be Prepared as Shown in Scheme 15. Reductive alkylation of the commercially available amine (XXXVIII) with tetrahydropyran-4-one (III) using for example sodium triacetoxyborohydride in dichloroethane provides the intermediate (XXXIX) which is deprotected using HCl in ethanol or trifluoroacetic acid to afford the primary amine (XXVII).

Scheme 15.

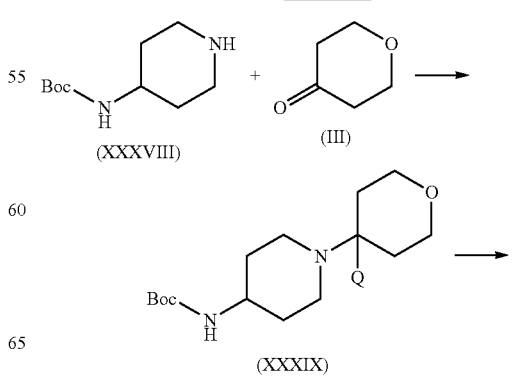

(XXXVIII)  (III)

(XXXIX)

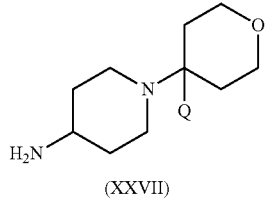

(XXVII)

The compounds of formula (I) are expected to be useful in the treatment of psychotic disorders or cognitive impairment.

The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term psychotic disorder includes Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9);

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90);

Anxiety disorders including Social Anxiety Disorder, Panic Attack, Agoraphobia, Panic Disorder, Agoraphobia Without History of Panic Disorder (300.22), Specific Phobia (300.29) including the subtypes Animal Type, Natural Environment Type, Blood-Injection-Injury Type, Situational Type and Other Type), Social Phobia (300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder and Anxiety Disorder Not Otherwise Specified (300.00);

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide;

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition; and Substance-Induced Sleep Disorder including the subtypes Insomnia Type, Hypersomnia Type, Parasomnia Type and Mixed Type;

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; and Eating Disorder Not Otherwise Specified (307.50);

Autistic Disorder (299.00); Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23);

Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9); and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

The compounds of Formula (I) are also expected to be useful for the enhancement of cognition, including both the treatment of cognitive impairment on its own and the treatment of cognitive impairment in other diseases such as schizophrenia, bipolar disorder, depression, other psychiatric disorders and psychotic conditions associated with cognitive impairment.

Within the context of the present invention, the term cognitive impairment includes, for example, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

The therapy of the present invention may also be used as a memory and/or cognition enhancer in healthy humans with no cognitive and/or memory deficit.

In a further aspect therefore, the invention provides a compound of formula (I) as hereinbefore described or a salt or solvate thereof for use in therapy.

In another aspect, the invention provides a compound of formula (I) or a salt or solvate thereof for use in the treatment of a condition which requires agonism of a muscarinic $M_1$ receptor.

In another aspect, the invention provides a compound of formula (I) as hereinbefore described or a salt or solvate thereof for use in the treatment of a psychotic disorder. The invention also provides a compound of formula (I) as hereinbefore described or a salt or solvate thereof for use in the treatment of cognitive impairment.

In another aspect, the invention provides the use of a compound of formula (I) as hereinbefore described or a salt or solvate thereof in the manufacture of a medicament for the treatment of a condition which requires agonism of a muscarinic $M_1$ receptor.

In another aspect, the invention provides the use of a compound of formula (I) as hereinbefore described or a salt or solvate thereof in the manufacture of a medicament for the treatment of a psychotic disorder. The invention also provides the use of a compound of formula (I) as hereinbefore described or a salt or solvate thereof in the manufacture of a medicament for the treatment of cognitive impairment.

In another aspect, the invention provides a method of treating a condition which requires agonism of a muscarinic $M_1$ receptor, which comprises administering to a mammal in need thereof an effective amount of a compound of formula (I) as hereinbefore described or a salt or solvate thereof.

In another aspect, the invention provides a method of treating a psychotic disorder which comprises administering to a mammal in need thereof an effective amount of a compound of formula (I) as hereinbefore described or a salt or solvate thereof. The invention also provides a method of treating cognitive impairment, which comprises administering to a mammal in need thereof an effective amount of a compound of formula (I) as hereinbefore described or a salt or solvate thereof.

The compounds of formula (I) and their salts and solvates thereof may also be suitable for combination with other actives, such as typical and atypical antipsychotics, mood stabilisers, antidepressants, anxiolytics, drugs for extrapyrimidal side effects and cognitive enhancers to provide improved treatment of psychotic disorders.

The combination therapies of the invention are, for example, administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) or a salt or solvate thereof and at least one antipsychotic agent, a mood stabiliser, an antidepressant, an anxiolytic, a drug for extrapyrimidal side effects or a cognitive enhancer are within the scope of the current invention. In one embodiment of adjunctive therapeutic administration as described herein, a patient is typically stabilised on a therapeutic administration of one or more of the components for a period of time and then receives administration of another component. The compounds of formula (I) or a salt or solvate thereof may be administered as adjunctive therapeutic treatment to patients who are receiving administration of at least one antipsychotic agent, a mood stabiliser, an antidepressant, an anxiolytic, a drug for extrapyrimidal side effects or a cognitive enhancer, but the scope of the invention also includes the adjunctive therapeutic administration of at least one antipsychotic agent, a mood stabiliser, an antidepressant, an anxiolytic, a drug for extrapyrimidal side effects or a cognitive enhancer to patients who are receiving administration of compounds of formula (I) or a salt or solvate thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of compounds of formula (I) or a salt or solvate thereof to a patient receiving therapeutic administration of at least one antipsychotic agent. In a further aspect, the invention provides the use of compounds of formula (I) or a salt or solvate thereof in the manufacture of a medicament for adjunctive therapeutic administration for the treatment of a psychotic disorder in a patient receiving therapeutic administration of at least one antipsychotic agent. The invention further provides compounds of formula (I) or a salt or solvate thereof for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I) or a salt or solvate thereof. In a further aspect, the invention provides the use of at least one antipsychotic agent in the manufacture of a medicament for adjunctive therapeutic administration for the treatment of a psychotic disorder in a patient receiving therapeutic administration of compounds of formula (I) or a salt or solvate thereof. The invention further provides at least one antipsychotic agent for adjunctive therapeutic administration for the treatment of a psychotic disorder in a patient receiving therapeutic administration of compounds of formula (I) or a salt or solvate thereof.

In a further aspect, the invention provides a method of treatment of a psychotic disorder by simultaneous therapeutic administration of compounds of formula (I) or a salt or solvate thereof in combination with at least one antipsychotic agent. The invention further provides the use of a combination of compounds of formula (I) or a salt or solvate thereof and at least one antipsychotic agent in the manufacture of a medicament for simultaneous therapeutic administration in the treatment of a psychotic disorder. The invention further provides the use of compounds of formula (I) or a salt thereof in the manufacture of a medicament for simultaneous therapeutic administration with at least one antipsychotic agent in the treatment of a psychotic disorder. The invention further provides compounds of formula (I) or a salt thereof for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) or a salt thereof in the treatment of a psychotic disorder.

In a further aspect, the invention provides a kit-of-parts for use in the treatment of a psychotic disorder comprising a first dosage form comprising compounds of formula (I) or a salt or solvate thereof and one or more further dosage forms each comprising a antipsychotic agent for simultaneous therapeutic administration.

In another aspect, the invention provides a method of treatment of a psychotic disorder by adjunctive therapeutic administration of a compound of the present invention to a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides the use of a compound of the present invention in the manufacture of a medicament for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention also provides the use of a compound of the present invention in adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

The invention further provides the use of a compound of the present invention for use for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyrimidal side effects and a cognitive enhancer.

In a further aspect, the invention provides a method of treatment of a psychotic disorder by adjunctive therapeutic administration of an active ingredient selected from the group consisting of: a mood stabiliser, an antidepressant, an anxiolytic, a drug for extrapyrimidal side effects and a cognitive enhancer to a patient receiving therapeutic administration of a compound of the present invention.

In a further aspect, the invention provides the use of an active ingredient selected from the group consisting of: a mood stabiliser, an antidepressant, an anxiolytic, a drug for extrapyrimidal side effects and a cognitive enhancer in the manufacture of a medicament for adjunctive therapeutic administration for the treatment of a psychotic disorder in a patient receiving therapeutic administration of a compound of the present invention.

The invention also provides the use of an active ingredient selected from the group consisting of: a mood stabiliser, an antidepressant, an anxiolytic, a drug for extrapyrimidal side effects and a cognitive enhancer for adjunctive therapeutic administration for the treatment of a psychotic disorder in a patient receiving therapeutic administration of a compound of the present invention.

In a further aspect, the invention provides a method of treatment of a psychotic disorder by simultaneous therapeutic administration of a compound of the present invention in combination with an active ingredient selected from the group consisting of: a mood stabiliser, an antidepressant, an anxiolytic, a drug for extrapyrimidal side effects and a cognitive enhancer.

The invention further provides the use of a combination of a compound of the present invention and an active ingredient selected from the group consisting of: a mood stabiliser, an antidepressant, an anxiolytic, a drug for extrapyrimidal side effects and a cognitive enhancer in the manufacture of a medicament for simultaneous therapeutic administration in the treatment of a psychotic disorder.

The invention further provides the use of a combination of a compound of the present invention and an active ingredient selected from the group consisting of: a mood stabiliser, an antidepressant, an anxiolytic, a drug for extrapyrimidal side effects and a cognitive enhancer for simultaneous therapeutic administration in the treatment of a psychotic disorder.

The invention further provides the use of a compound of the present invention in the manufacture of a medicament for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides the use of a compound of the present invention for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides a compound of the present invention for use for simultaneous therapeutic administration with an active ingredient selected from the group consisting of: a mood stabiliser, an antidepressant, an anxiolytic, a drug for extrapyrimidal side effects and a cognitive enhancer in the treatment of a psychotic disorder.

The invention further provides the use of an active ingredient selected from the group consisting of: a mood stabiliser, an antidepressant, an anxiolytic, a drug for extrapyrimidal side effects and a cognitive enhancer in the manufacture of a medicament for simultaneous therapeutic administration with a compound of the present invention in the treatment of a psychotic disorder.

The invention further provides the use of an active ingredient selected from the group consisting of: a mood stabiliser, an antidepressant, an anxiolytic, a drug for extrapyrimidal side effects and a cognitive enhancer for simultaneous therapeutic administration with a compound of the present invention in the treatment of a psychotic disorder.

In a further aspect, the invention provides a kit-of-parts for use in the treatment of a psychotic disorder comprising a first dosage form comprising a compound of the present invention and one or more further dosage forms each comprising an active ingredient selected from the group consisting of: a mood stabiliser, an antidepressant, an anxiolytic, a drug for extrapyrimidal side effects and a cognitive enhancer for simultaneous therapeutic administration.

Examples of antipsychotic drugs that may be useful in the present invention include, but are not limited to: sodium channel blockers; mixed 5HT/dopamine receptor antagonists; mGluR5 positive modulators; D3 antagonists; 5HT6 angatonists; nicotinic alpha-7 modulators; glycine transporter GlyT1 inhibitors; D2 partial agonist/D3 antanogist/H3 antagonists; AMPA modulators; NK3 antagonists such as osanetant and talnetant; an atypical antipsychotic, for example clozapine, olanzapine, risperidone, quetiapine, aripirazole, ziprasidone and amisulpride; butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs that may be suitable for use in the present invention are as follows: clozapine (available under the tradename CLOZARIL®, from Mylan, Zenith Goldline, UDL, Novartis); olanzapine (available under the tradename ZYPREXA®, from Lilly; ziprasidone (available under the tradename GEODON®, from Pfizer); risperidone (available under the tradename RISPERDAL®, from Janssen); quetiapine fumarate (available under the tradename SEROQUEL®, from AstraZeneca); sertindole (available under the tradename SERLECT®); amisulpride (available under the tradename SOLION®, from Sanofi-Synthelabo); haloperidol (available under the tradename HALDOL®, from Ortho-McNeil); haloperidol decanoate (available under the tradename HALDOL Decanoate®); haloperidol lactate (available under the tradenames HALDOL® and INTENSOL®); chlorpromazine (available under the tradename THORAZINE®, from SmithKline Beecham (GSK); fluphenazine (available under the tradename PROLIXIN®, from Apothecon, Copley, Schering, Teva, and American Pharmaceutical Partners, Pasadena); fluphenazine decanoate (available under the tradename PROLIXIN Decanoate®); fluphenazine enanthate (available under the tradename PROLIXIN®); fluphenazine hydrochloride (available under the tradename PROLIXIN®); thiothixene (available under the tradename NAVANE®;, from Pfizer); thiothixene hydrochloride (available under the tradename NAVANE®); trifluoperazine (10-[3-(4-methyl-1-piperazinyl)propyl]-2-(trifluoromethyl)phenothiazine dihydro chloride, available under the tradename STELAZINE®, from SmithKline Beckman; perphenazine (available under the tradename TRILAFON®; from Schering); perphenazine and amitriptyline hydrochloride (available under the tradename ETRAFON TRILAFON®); thioridazine (available under the tradename MELLARIL®; from Novartis, Roxane, HiTech, Teva, and Alpharma); molindone (available under the tradename MOBAN®, from Endo); molindone hydrochloride (available under the tradename MOBAN®); loxapine (available under the tradename LOXITANE®; from Watson); loxapine hydrochloride (available under the tradename LOXITANE®); and loxapine succinate (available under the tradename LOXITANE®). Furthermore, benperidol (Glianimon®), perazine (Taxilan®) or melperone (Eunerpan®)) may be used.

Other suitable antipsychotic drugs include promazine (available under the tradename SPARINE®), triflurpromazine (available under the tradename VESPRIN®), chlorprothixene (available under the tradename TARACTAN®), droperidol (available under the tradename INAPSINE®), acetophenazine (available under the tradename TINDAL®;), prochlorperazine (available under the tradename COMPAZINE®), methotrimeprazine (available under the tradename NOZINAN®), pipotiazine (available under the tradename PIPOTRIL®), iloperidone, pimozide and flupenthixol.

The antipsychotic drugs listed above by Tradename may also be available from other suppliers under a different Tradename.

In one further aspect of the invention, suitable antipsychotic agents include olanzapine, risperidone, quetiapine, aripiprazole, haloperidol, clozapine, ziprasidone, talnetant and osanetant.

Mood stabilisers which may be used in the therapy of the present invention include lithium, sodium valproate/valproic acid/divalproex, carbamazepine, lamotrigine, gabapentin, topiramate, oxcarbazepine and tiagabine.

Antidepressant drugs which may be used in the therapy of the present invention include serotonin antagonists, CRF-1 antagonists, Cox-2 inhibitor/SSRI dual antagonists; dopamine/noradrenaline/serotonin triple reuptake inhibitors; NK1 antagonists; NK1 and NK2 dual antagonists; NK1/SSRI dual antagonists; NK2 antagonists; serotonin agonists (such as rauwolscine, yohimbine and metoclopramide); serotonin reuptake inhibitors (such as citalopram, escitalopram, fluoxetine, fluvoxamine, femoxetine, indalpine, zimeldine, paroxetine and sertraline); dual serotonin/noradrenaline reuptake inhibitors (such as venlafaxine, reboxetine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); 5HT3 antagonists (such as example ondansetron and granisetron); and others (such as bupropion, amineptine, radafaxine, mianserin, mirtazapine, nefazodone and trazodone).

Anxiolytics which may be used in the therapy of the present invention include V1b antagonists, 5HT7 antagonists and benzodiazepines such as alprazolam and lorazepam.

Drugs for extrapyramidal side effects which may be used in the therapy of the present invention include anticholinergics (such as benztropine, biperiden, procyclidine and trihexyphenidyl), antihistamines (such as diphenhydramine) and dopaminergics (such as amantadine).

Cognitive enhancers which may be used in the therapy of the present invention include example cholinesterase inhibitors (such as tacrine, donepezil, rivastigmine and galantamine), H3 antagonists and muscarinic M1 agonists (such as cevimeline).

In one embodiment, the active ingredient for use in combination with a compound of the present invention, is an atypical antipsychotic, for example clozapine, olanzapine, risperidone, quetiapine, aripirazole, ziprasidone or amisulpride.

In one embodiment, the active ingredient for use in combination with a compound of the present invention is a typical antipsychotic, for example chlorpromazine, thioridazine, mesoridazine, fluphenazine, perphenazine, prochlorperazine, trifluoperazine, thiothixine, haloperidol, thiflurpromazine, pimozide, droperidol, chlorprothixene, molindone or loxapine.

In another embodiment, the active ingredient for use in combination with a compound of the present invention is a mood stabiliser, for example lithium, sodium valproate/valproic acid/divalproex, carbamazepine, lamotrigine, gabapentin, topiramate, oxcarbazepine or tiagabine.

In another embodiment, the active ingredient for use in combination with a compound of the present invention is an antidepressant, for example a serotonin agonist (such as rauwolscine, yohimbine or metoclopramide); a serotonin reuptake inhibitor (such as citalopram, escitalopram, fluoxetine, fluvoxamine, femoxetine, indalpine, zimeldine, paroxetine or sertraline); a dual serotonin/noradrenaline reuptake inhibitor (such as venlafaxine, reboxetine, duloxetine or milnacipran); a noradrenaline reuptake inhibitors (such as reboxetine); a tricyclic antidepressants (such as amitriptyline, clomipramine, imipramine, maprotiline, nortriptyline or trimipramine); a monoamine oxidase inhibitor (such as isocarboxazide, moclobemide, phenelzine or tranylcypromine); or other (such as bupropion, amineptine, radafaxine, mianserin, mirtazapine, nefazodone or trazodone).

In another embodiment, the active ingredient for use in combination with a compound of the present invention is an anxiolytic, for example a benzodiazepine such as alprazolam or lorazepam.

For use in medicine, the compounds of the present invention are usually administered as a standard pharmaceutical composition. The present invention therefore provides in a further aspect a pharmaceutical composition comprising a compound of formula (I) as hereinbefore described or a salt or solvate thereof and a pharmaceutically acceptable carrier. The pharmaceutical composition can be for use in the treatment of any of the conditions described herein.

The compounds of formula (I) may be administered by any convenient method, for example by oral, parenteral (e.g.

intravenous), buccal, sublingual, nasal, rectal or transdermal administration and the pharmaceutical compositions adapted accordingly.

The compounds of formula (I) as hereinbefore described and their salts or solvates which are active when given orally can be formulated as liquids or solids, for example syrups, suspensions or emulsions, tablets, capsules and lozenges.

A liquid formulation will generally consist of a suspension or solution of the compound or salt or solvate in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt or solvate in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. The composition may be in unit dose form such as a tablet, capsule or ampoule.

Each dosage unit for oral administration contains, for example, from 1 to 250 mg (and for parenteral administration contains, for example, from 0.1 to 25 mg) of a compound of the formula (I) or a salt thereof calculated as the free base.

The compounds of the invention will normally be administered in a daily dosage regimen (for an adult patient) of, for example, an oral dose of between 1 mg and 500 mg, such as between 10 mg and 400 mg, e.g. between 10 and 250 mg or an intravenous, subcutaneous, or intramuscular dose of between 0.1 mg and 100 mg, such as between 0.1 mg and 50 mg, e.g. between 1 and 25 mg of the compound of the formula (I) or a salt thereof calculated as the free base, the compound being administered 1 to 4 times per day. Suitably the compounds will be administered for a period of continuous therapy, for example for a week or more.

The antipsychotic agent component or components used in the adjunctive therapy of the present invention may also be administered in their basic or acidic forms as appropriate or, where appropriate, in the form of a salt or other derivative. All solvates and all alternative physical forms of the antipsychotic agent or agents or their salts or derivatives as described herein, including but not limited to alternative crystalline forms, amorphous forms and polymorphs, are also within the scope of this invention. In the case of the antipsychotic agent or agents, the forms and derivatives are, for example, those which are approved for therapeutic administration as monotherapies, including those mentioned above, but all references to antipsychotic agents herein include all salts or other derivatives thereof, and all solvates and alternative physical forms thereof.

For adjunctive therapeutic administration according to the invention, compounds of formula (I) or salts or solvates and the antipsychotic agent or agents or their salts, derivatives or solvates may each be administered in pure form, but each of the components will, for example, be formulated into any suitable pharmaceutically acceptable and effective composition which provides effective levels of the respective component in the body. The choice of the most appropriate pharmaceutical compositions for each component is within the skill of the art, and may be the same form or different forms for each of the components. Suitable formulations include, but are not limited to tablets, capsules, powders, granules, lozenges, suppositories, reconstitutable powders, or liquid preparations such as oral or sterile parenteral solutions or suspensions.

For simultaneous administration as a combined composition of compounds of formula (I) and the antipsychotic agent or agents according to the invention, compounds of formula (I) or their salts or solvates and the antipsychotic agent or agents and their salts, derivatives or solvates may be administered together in pure form, but the combined components will, for example, be formulated into any suitable pharmaceutically acceptable and effective composition which provides effective levels of each of the components in the body. The choice of the most appropriate pharmaceutical compositions for the combined components is within the skill of the art. Suitable formulations include, but are not limited to tablets, sub-lingual tablets, buccal compositions, capsules, powders, granules, lozenges, suppositories, reconstitutable powders, or liquid preparations such as oral or sterile parenteral solutions or suspensions.

In order to obtain consistency of adjunctive administration, the compositions of each of the components, or of the combination of the components is, for example, in the form of a unit dose.

The term "treatment" includes prophylaxis, where this is appropriate for the relevant condition(s).

Biological Test Methods

FLIPR Experiments on $M_1$ Receptor to Determine Agonist/Antagonist Potency

Compounds of the invention were characterized in a functional assay to determine their ability to activate the intracellular calcium pathway in CHO cells with stable expression of human muscarinic receptors using FLIPR (Fluorometric Imaging Plate Reader) technology. Briefly, CHO-M1 cells were plated (20,000/well) and allowed to grow overnight at 37 degrees. Media was removed and 30 uL loading buffer containing FLIPR Calcium 3 dye (Molecular Devices Co., Sunnyvale, Calif.) was added according to manufacturer's instructions. After incubation at 37 degrees for 45-60 minutes, 10 uL of the assay buffer containing test compounds was added to each well on FLIPR instrument. Calcium response was monitored to determine agonism. Plates were then incubated for another 10-15 minutes before 10 uL of assay buffer containing acetylcholine was added as the agonist challenge. Calcium response was then monitored again to determine compound's antagonism to acetylcholine. Concentration-response curves of both agonism and antagonism on M1 receptors were performed for each compound. Results were imported into ActivityBase data analysis suite (ID Business Solution Inc., Parsippany, N.J.) where the curves were analysed by non-linear curve fitting and the resulting pEC50/pIC50 were calculated.

FLIPR Experiments on $M_1$ Receptor to Determine Agonist Intrinsic Activity

To determine the intrinsic activities of M1 agonist compounds, compounds of the invention were characterized in FLIPR experiments on U2OS cells with transient expression of human muscarinic M1 receptors. Briefly, U2OS cells were transduced with M1 BacMam virus (#) in $2 \times 10 \, e^5$/mL cell suspension with 0.1% virus/cell ratio (v/v). The virus to cell ratio was determined in separate experiments by functional titration to be most appropriate to measure intrinsic activities of partial agonists. After mixing with virus in suspension, cells were then plated (10,000/well) and allowed to grow overnight at 37 degrees. FLIPR experiment was then carried out next day using the same protocol as described above for CHO-M1 cells. Results were imported into ActivityBase data analysis suite where the curves were analysed by non-linear curve fitting and the resulting pEC50 values were calculated. The intrinsic activities of agonist compounds were calculated as percentage of maximum FLIPR response induced by acetylcholine added as control on the same compound plates, and converted to a fraction between 0 and 1.

: Ames, R S; Fornwald, J A; Nuthulaganti, P; Trill, J J; Foley, J J; Buckley, P T; Kost, T A; Wu, Z and Romanos, M A. (2004) Use of BacMam recombinant baculoviruses to support G protein-coupled receptor drug discovery. Receptors and Channels 10 (3-4): 99-109

The exemplified compounds have a pEC$_{50}$ value of >6.0 at the muscarinic $M_1$ receptor, and intrinsic activity >0.5.

FLIPR Experiments on $M_{2-5}$ Receptor to Determine Receptor Subtype Selectivity To determine selectivity of compounds of the invention against other muscarinic receptor subtypes, compounds were characterized in FLIPR experiments in CHO cells with stable expression of human muscarinic receptors, M2, M3, M4 or M5. In the case of M2 and M4 receptors, chimeric G-protein Gqi5 was also co-expressed to couple receptors to the calcium signaling pathway. Briefly, cells were plated (20,000/well) and allowed to grow overnight at 37 degrees. FLIPR experiment was then carried out next day using the same protocol as described above for CHO-M1 cells. Results were imported into ActivityBase data analysis suite where the curves were analysed by non-linear curve fitting and the resulting pEC50/pIC50 values were calculated.

The exemplified compounds are selective for the M1 receptor over M2, M3, M4 and M5 receptors, with typical selectivity (ratio of pEC50's) of ≧10-fold, and in certain cases ≧100-fold.

The invention is further illustrated by the following non-limiting examples.

MDAP refers to mass-directed automated purification using reverse phase chromatography on $C_{18}$ stationary phase eluted with acetonitrile/water/0.1% formic acid.

SCX refers to a sulfonic acid ion exchange resin supplied by Varian.

All reactions were either done under argon or can be done under argon, unless stated otherwise (for example hydrogenation reactions).

Description 1

2-Fluoro-6-iodo-4-methylaniline (D1)

A solution of 2-fluoro-4-methylaniline (1.0 g, 8 mmol) (bought from Avocado, Lancaster or Aldrich) in glacial acetic acid (10 ml) was treated with sodium acetate trihydrate (2.2 g, 16 mmol) then iodine monochloride (1.3 g). After 30 min at room temperature aqueous sodium bicarbonate/sodium sulfite and diethyl ether were added, and the organic phase was dried (MgSO$_4$), evaporated and chromatographed on silica eluting with 0 to 30% ethyl acetate in hexane to give the title compound, 370 mg.

Description 2

1-Fluoro-3-iodo-2-isocyanato-5-methylbenzene (D2)

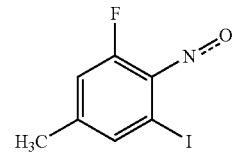

A mixture of 2-fluoro-6-iodo-4-methylaniline (D1) (370 mg, 1.5 mmol), triphosgene (150 mg, 0.05 mmol), and dioxan (3 ml) was heated at reflux for 1 h 15 min then cooled and evaporated to give the crude title compound.

Description 3

1,1-Dimethylethyl 4-({[(2-fluoro-6-iodo-4-methylphenyl)amino]-carbonyl}amino)-1-piperidinecarboxylate (D3)

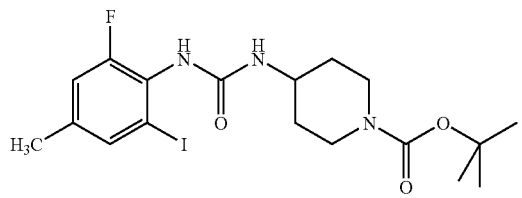

A mixture of the crude 1-fluoro-3-iodo-2-isocyanato-5-methylbenzene from description D2, 4-amino-1-N-Boc piperidine (200 mg, 1 mmol), and dichloromethane (3 ml) was stirred at room temperature for 1 h then directly purified by chromatography on silica gel eluting with 0 to 10% methanol in dichloromethane. Further purification by MDAP (mass-directed auto-purification) gave the title compound 300 mg.

Description 4

1,1-Dimethylethyl 4-(4-fluoro-6-methyl-2-oxo-2,3-dihydro-1H-benzimidazol-1-yl)-1-piperidinecarboxylate (D4)

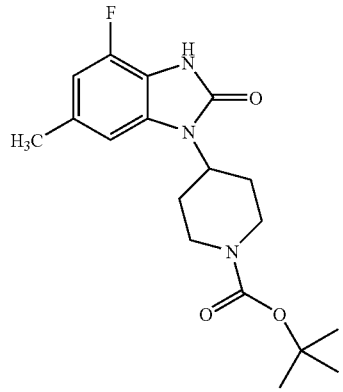

D4

Under an argon atmosphere, a mixture of 1,4-dioxane (3 ml), palladium 1,1'-bis(diphenylphosphino)ferrocene dichloride (10% mol, 0.0623 mmol, ~x50 mg), Na$^t$BuO (2 eq., 1.26 mmol, 121 mg), were sonicated for 10 minutes at room temperature and 1,1-dimethylethyl 4-({[(2-fluoro-6-iodo-4-methylphenyl)amino]carbonyl}amino)-1-piperidine-carboxylate (D3) (1 eq., 0.623 mmol, 300 mg) was added at room temperature and the mixture was refluxed at 80° C. for one overnight. The reaction mixture was cooled to room temperature, poured onto NH$_4$Cl (saturated solution) and the aqueous solution obtained was extracted with ethyl acetate repeatedly; the organics were combined, dried over Na$_2$SO$_4$, filtered and the solvent was evaporated to afford the crude compound (250 mg) that was purified by MDAP to yield the title compound, 30 mg, 11%.

$^1$H NMR [] (DMSO, 400 MHz) 1.44 (9H, s), 1.68 (2H, d broad), 2.20 (2H, dddd), 2.32 (3H, s), 2.85 (2H, s broad), 4.05 (2H, m broad), 4.30 (1H, m broad), 6.72 (1H, d), 6.90 (1H, s), 11.3 (1H, s broad).

Description 4a

Scale-Up Procedure 1,1-Dimethylethyl 4-(4-fluoro-6-methyl-2-oxo-2,3-dihydro-1H-benzimidazol-1-yl)-1-piperidinecarboxylate (D4a)

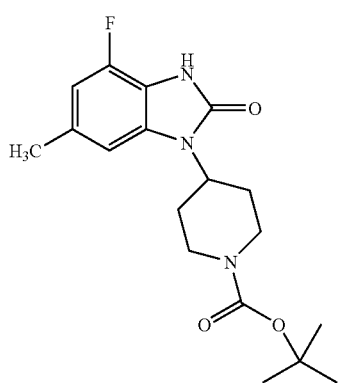

D4a

Under an argon atmosphere, bis(3,5,3',5'-dimethoxy-dibenzylideneacetone) palladium (0) (6% mol, 1.1 mmol, 0.9 g), 1,1'-bis(diphenylphosphino)ferrocene (6% mol, 0.61 g), Na$^t$BuO (2 eq., 36 mmol, 3.5 g), were all dissolved in 1,4-dioxane (40 ml) and the system was purged through with argon. The mixture was stirred at room temperature for 15 minutes and 1,1-dimethylethyl 4-({[(2-bromo-6-fluoro-4-methylphenyl)amino]-carbonyl}amino)-1-piperidinecarboxylate (D32) (7.7 g, 17.9 mmol) was added at room temperature and the mixture was heated to 80° C. for 1.5 hours and then to 100° C. for extra 2 hours; the mixture was then cooled to room temperature, diluted with ethyl acetate and the organic phase obtained was washed with water and brine. Organics were dried over Na$_2$SO$_4$, filtered and the solvent was evaporated to afford the crude product that was purified by chromatography (ethyl acetate-n-hexane) to afford the title compound, 4.3 g, 70%, pale-grey solid, M$^+$-H=348.

Description 5

4-Fluoro-6-methyl-1-(4-piperidinyl)-1,3-dihydro-2H-benzimidazol-2-one hydrochloride (D5)

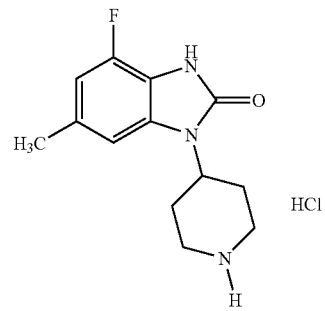

D5

1,1-Dimethylethyl 4-(4-fluoro-6-methyl-2-oxo-2,3-dihydro-1H-benzimidazol-1-yl)-1-piperidinecarboxylate D4 (0.072 mmol, 25 mg) was dissolved in dichloromethane (5 ml) and was treated with HCl (3 ml of a 4M solution in 1,4-dioxane) at room temperature; the mixture was stirred at room temperature for two hours. Solvent was evaporated to afford the title compound, mono hydrochloride salt, M$^+$+H=250.

Description 5a

Scale-Up Procedure

4-Fluoro-6-methyl-1-(4-piperidinyl)-1,3-dihydro-2H-benzimidazol-2-one hydrochloride (D5a)

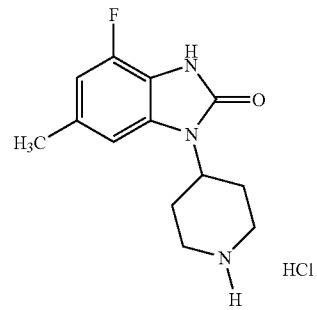

D5a 1,1-Dimethylethyl 4-(4-fluoro-6-methyl-2-oxo-2,3-dihydro-1H-benzimidazol-1-yl)-1-piperidinecarboxylate (~12.3 mmol, 4.3 g) (D4a) was dissolved in dichloromethane/methanol (50 ml/20 ml) and was treated with HCl (10 eq., 0.123 mol, 30 ml of a 4M solution in 1,4-dioxane) at room temperature; the mixture was stirred at room temperature for one overnight. Solvent was evaporated and the solid obtained was triturated with diethyl ether to afford the title compound (3.5 g, about 12.3 mmol brown solid) as the mono hydrochloride salt, M⁺+H=250.

Description 6

1-Bromo-5-chloro-3-fluoro-2-isocyanatobenzene (D6)

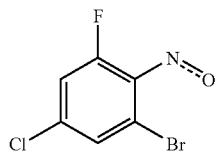

2-Bromo-4-chloro-6-fluoroaniline (5 mmol, 1.125 g), bis(trichloromethyl)carbonate (1.7 mmol, 0.50 g) and 1,4-dioxane (10 ml) were mixed together and the mixture was heated to 100° C. for 15 minutes; the mixture was then cooled to room temperature and it was filtered. The filtrate was concentrated to afford a mixture of products (2.2 g) containing the title compound, M⁺+MeO=283 (LC-MS run in methanol).

Description 7

1,1-Dimethylethyl 4-({[(2-bromo-4-chloro-6-fluorophenyl)amino]-carbonyl}amino)-1-piperidinecarboxylate (D7)

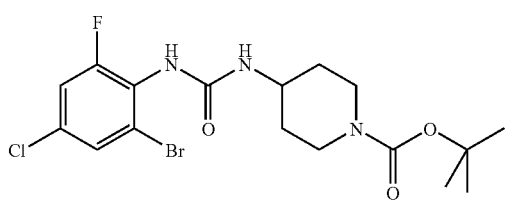

1-Bromo-5-chloro-3-fluoro-2-isocyanatobenzene (D6) (4.4 mmol, 1.1 g) and 1,1-dimethylethyl 4-amino-1-piperidinecarboxylate (1 eq., 4.4 mmol, 0.88 g) were mixed together. Dichloromethane (5 ml) was added to the mixture at room temperature for 1 hour. THF (5 ul) was added at room temperature for one hour. Solvent was subsequently evaporated and the crude obtained was purified by chromatography to afford the title compound, 0.6 g, 30%.

¹H NMR DMSO, 400 MHz) 1.26 (2H, m), 1.39 (9H, s), 1.77 (2H, dd), 2.86 (2H, s broad), 3.60 (1H, m), 4.03 (2H, d), 6.48 (1H, d), 7.59 (1H, dd), 7.65 (1H, t), 7.78 (1H, s).

Description 8

1,1-Dimethylethyl 4-(6-chloro-4-fluoro-2-oxo-2,3-dihydro-1H-benzimidazol-1-yl)-1-piperidinecarboxylate (D8)

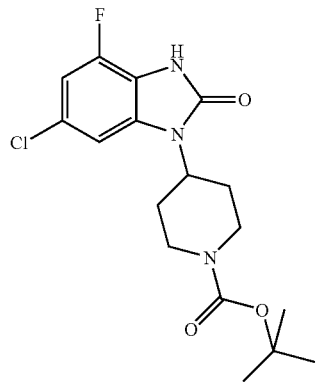

Under an argon atmosphere, 1,1-dimethylethyl 4-({[(2-bromo-4-chloro-6 fluorophenyl)amino]carbonyl}amino)-1-piperidinecarboxylate (D7) (1.09 mmol, 0.493 g), 1,4-dioxane (4.4 ml), Pd₂dba₃ (0.05 eq., 0.054 mmol, 50 mg), BINAP (0.055 eq., 0.059 mmol, 37 mg), Na^tBuO (1.5 eq., 1.63 mmol, 157 mg) were mixed together and heated to 80° C. under argon for 4 days. The reaction mixture was cooled to room temperature, quenched with water and the aqueous solution obtained was extracted with ethyl acetate. The solvent was evaporated and the crude was purified by MDAP. Fractions were collected and the solvent evaporated to yield the title compound, 15 mg, 3%, M⁺-H=368.

Description 9

6-Chloro-4-fluoro-1-(4-piperidinyl)-1,3-dihydro-2H-benzimidazol-2-one hydrochloride (D9)

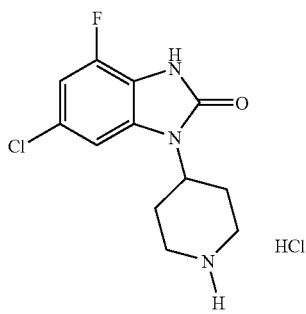

1,1-Dimethylethyl 4-(6-chloro-4-fluoro-2-oxo-2,3-dihydro-1H-benzimidazol-1-yl)-1-piperidinecarboxylate (D8) (0.203 mmol, 75 mg) and HCl (233 microliters of a 4M solution in 1,4-dioxane) were mixed together and stirred at room temperature for two hours. Solvent was evaporated to afford the title compound, mono hydrochloride salt, complete conversion, M⁺+H=270.

Description 10

4-Nitro-3,5-difluorophenol (D10)

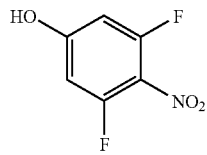

A solution of 3,5-difluorophenol (1.3 g, 10 mmol) in dichloromethane (50 ml) at 0° C. was treated with nitric acid (70%, 0.7 ml, 10 mmol). The cooling bath was removed and after 30 min at room temperature the solution washed with water then dried over MgSO$_4$, filtered and evaporated. The product was purified by silica gel chromatography eluting with 20 to 50% ethyl acetate in hexane to yield the title compound, 440 mg.

$^1$H NMR ☐ DMSO, 400 MHz): 6.7 (2H, d), and 11.8 (1H, bs).

Description 11

4-Nitro-3,5-difluoroanisole (D11)

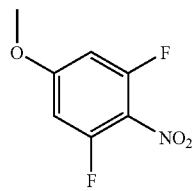

A mixture of 4-nitro-3,5-difluorophenol (D10) (440 mg, 2.5 mmol), potassium carbonate (600 mg, 4.6 mmol), iodomethane (1 ml), and dimethylformamide (5 ml) stirred overnight at room temperature then ethyl acetate and water added and the solution washed with water then dried over MgSO$_4$, filtered and evaporated to yield the title compound, pale brown oil, 370 mg.

$^1$H NMR ☐ DMSO, 400 MHz): 3.9 (3H, s) and 7.1 (2H, d).

Description 12

1,1-Dimethylethyl 4-[(2-nitro-3-fluoro-5-methoxyphenyl)amino]-piperidinecarboxylate (D12)

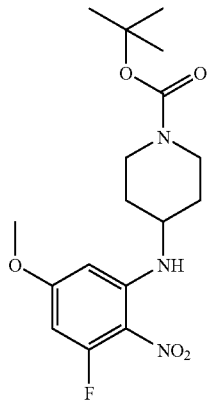

4-Nitro-3,5-difluoroanisole (D11) (370 mg, 2 mmol) was dissolved in dry dimethylformamide (3 ml) and diisopropylethylamine (0.4 ml), and 1,1-dimethylethyl 4-amino-1-piperidinecarboxylate (400 mg, 2 mmol) were added at room temperature. The mixture was stirred at room temperature for 18 h, then cooled to room temperature and water and ethyl acetate added. The organic layer was dried over MgSO$_4$, filtered and evaporated, and the residue crystallised from diethyl ether to afford the title compound, 380 mg. M$^-$–H=368.

Description 13a 1,1-Dimethylethyl 4-[(2-amino-3-fluoro-5-methoxyphenyl)amino]-1-piperidinecarboxylate (D13a)

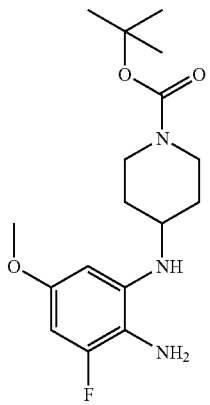

1,1-Dimethylethyl 4-[(2-nitro-3-fluoro-5-methoxyphenyl)amino]-piperidine-carboxylate (D12) (380 mg, 1 mmol) was dissolved in ethanol (10 ml) and Raney nickel (50% aqueous suspension, 1 ml) was added at room temperature; the mixture was heated to 40° C. and hydrazine monohydrate (0.5 ml) was added over dropwise. After 30 min more, the reaction mixture was cooled to room temperature, filtered through Celite and the solvent evaporated. The product was purified by silica gel chromatography eluting with 20 to 50% ethyl acetate in hexane to yield the title compound, 250 mg. M$^+$-H=340.

Description 13b 1,1-Dimethylethyl 4-(4-fluoro-6-methoxy-2-oxo-2,3-dihydro-1H-benzimidazol-1-yl)-1-piperidinecarboxylate (D13b)

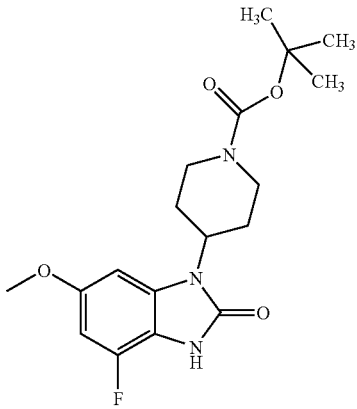

A mixture of 1,1-dimethylethyl 4-[(2-amino-3-fluoro-5-methoxyphenyl)amino]-1-piperidinecarboxylate (D13a) (230 mg, 0.7 mmol), carbonyl diimidazole (150 mg, 1.0 mmol), and tetrahydrofuran (6 ml) was heated 1 h at 50° C.

then partitioned between dichloromethane and water. The organic layer was purified by chromatography on silicagel eluting with 0 to 10% methanol in dichloromethane containing 0.2M ammonia to give the title compound as white crystals, 47%, 120 mg, M−-H=364.

Description 14

4-Fluoro-6-methoxy-1-(4-piperidinyl)-1,3-dihydro-2H-benzimidazol-2-one hydrochloride (D14)

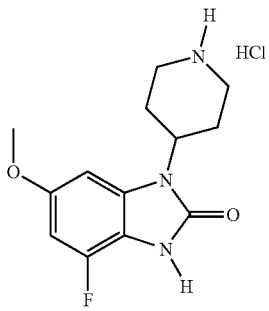

1,1-Dimethylethyl 4-(4-fluoro-6-methoxy)-2-oxo-2,3-dihydro-1H-benzimidazol-1-yl)-1-piperidinecarboxylate (D13b) (120 mg, 0.33 mmol) was dissolved in methanol (2 ml) and dichloromethane (1 ml) was treated with HCl (4M in 1,4-dioxane, 1 ml) at room temperature. The mixture was stirred at room temperature for 4 h. then evaporated to give the title compound, 100 mg. M+-H=266.

Description 15

Diethyl 2-(2,3-difluoro-4-nitrophenyl)malonate (D15)

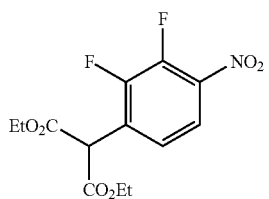

To diethyl malonate (5.1 g, 32 mmol) in N-methylpyrrolidone (50 ml) at 0° C. were added sodium hydride (1.6 g×60% in oil) then 2,3,4-trifluoronitrobenzene (5.4 g, 31 mmol) in more N-methylpyrrolidone (10 ml) at 20° C. After 2 h at room temperature the reaction was poured into aqueous ammonium chloride and extracted with ethyl acetate. Drying (MgSO$_4$), evaporation, and chromatography of a 10% sample of the product (20 g silica with 0-25% ethyl acetate in hexane) gave 0.5 g of a 1:1 mixture of the title compound and diethyl 2-(2,3-difluoro-6-nitrophenyl)malonate which was used directly in D16.

$^1$H NMR (DMSO, 400 MHz): 1.2 (6H, m), 4.2 (4H, m), 5.45 and 5.6 (1H, 2 s), 7.5 and 7.8 (1H, 2 m), 8.1 (1H, m).

Description 16

2,3-Difluoro-4-nitrophenylacetic acid (D16)

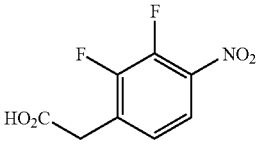

The mixture of diethyl 2-(2,3-difluoro-4-nitrophenyl)malonate and diethyl 2-(2,3-difluoro-6-nitrophenyl)malonate from D15 (0.5 g) was heated with 11M hydrochloric acid (5 ml) at reflux overnight then evaporated to give 320 mg of the title compound (pale yellow solid) as a 1:1 mixture with 2,3-difluoro-6-nitrophenylacetic acid. M−—CO$_2$H=172.

Description 17

2,3-Difluoro-4-nitrotoluene (D17)

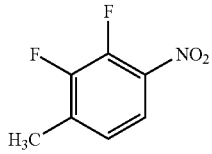

The mixture of 2,3-difluoro-4-nitrophenylacetic acid and 2,3-difluoro-6-nitrophenylacetic acid from D16 (13.5 g) was dissolved in dimethylformamide (100 ml) and potassium carbonate (8.5 g) added. After stirring at 50° C. for 30 min the cooled solution was partitioned between aqueous hydrochloric acid and hexane. Drying (MgSO$_4$), evaporation, and chromatography (0-5% ethyl acetate in hexane, 70 g silica column) gave 3.2 g of a 3:1 mixture of the title compound and 2,3-difluoro-6-nitrotoluene.

$^1$H NMR (DMSO, 400 MHz): 2.4 and 2.5 (3H, m), 7.3 and 7.6 (1H, 2 m), 7.9 (1H, m).

Description 18

2,3-difluoro-4-methylaniline (D18)

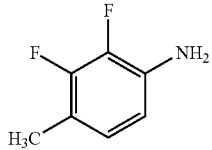

The mixture of 2,3-difluoro-4-aminotoluene and 2,3-difluoro-6-nitrotoluene from D17 (3.2 g, 18 mmol) was dissolved in ethanol (50 ml) and Raney nickel (5 ml×50% aqueous suspension) added. The mixture was heated to 40° C. and hydrazine hydrate (3.7 ml, 74 mmol) added in portions over 30 min. After 1 h more at 40° C. the mixture was cooled, filtered, and evaporated, and the residue partitioned between dichloromethane and water at pH9. Drying (MgSO$_4$), evaporation, and chromatography (0-25% ethyl acetate in hexane) gave 240 mg of the title compound.

¹H NMR (DMSO, 400 MHz): 2.5 (3H, m), 5.2 (2H, bs), 6.4 (1H, m), 6.7 (1H, m).

Description 19

2,3-Difluoro-6-iodo-4-methylaniline (D19)

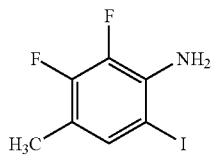

A solution of 2,3-difluoro-4-methylaniline (D19) (240 mg, 1.7 mmol) in glacial acetic acid (2 ml) was treated with sodium acetate trihydrate (440 mg, 3.2 mmol) then iodine monochloride (300 mg, 1.8 mmol). After 30 min at room temperature aqueous sodium bicarbonate/sodium sulfite and diethyl ether were added, and the organic phase was dried (MgSO$_4$) and evaporated to give the title compound, dark red gum (72%), 330 mg.

¹H NMR (DMSO, 400 MHz): 2.1 (3H, s), 5.2 (2H, bs), 7.3 (1H, d).

Description 20

2,3-Difluoro-6-iodo-4-methylphenyl isocyanate (D20)

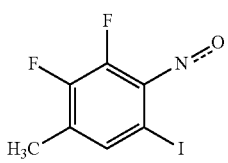

A mixture of 2,3-difluoro-6-iodo-4-methylaniline D19 (330 mg, 1.2 mmol), triphosgene (150 mg, 0.5 mmol), and dioxan (5 ml) was heated at 100° C. for 15 min then cooled and evaporated to give the crude title compound used directly in the next step.

Description 21

1,1-Dimethylethyl 4-({[(2,3-difluoro-6-iodo-4-methylphenyl)amino]-carbonyl}amino)-1-piperidinecarboxylate (D21)

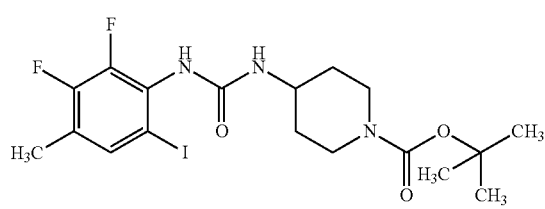

A mixture of the crude 2,3-difluoro-6-iodo-4-methylphenyl isocyanate from D20, 4-amino-1-N-Boc piperidine (480 mg), and dichloromethane (5 ml) was stirred at room temperature for 18 h then evaporated and directly purified by chromatography on silica gel 20 g eluting with 10-50% ethyl acetate in hexane to give the title compound, 300 mg. M⁻–H=494.

Description 22

1,1-Dimethylethyl 4-(4,5-difluoro-6-methyl-2-oxo-2,3-dihydro-1H-benzimidazol-1-yl)-1-piperidinecarboxylate (D22)

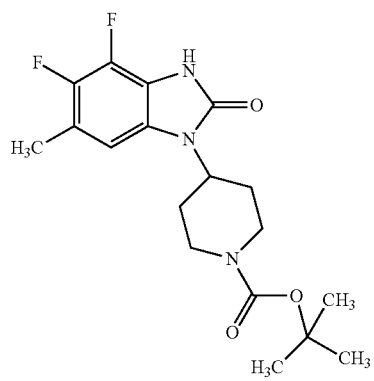

1,1-dimethylethyl 4-({[(2,3-difluoro-6-iodo-4-methylphenyl)amino]carbonyl}amino)-1-piperidine-carboxylate D21 was dissolved in 1 ml dioxan. Under an argon atmosphere, a mixture of 1,4-dioxane (3 ml), Pd$_2$dba$_3$ (35 mg, 0.4 mmol), Na$^t$BuO (120 mg, 1.20 mmol), and 1,1'-bis(diphenylphosphino)ferrocene (21 mg, 0.4 mmol) was stirred for 10 minutes at room temperature and then 1,1-dimethylethyl 4-({[(2,3-difluoro-6-iodo-4-methylphenyl)amino]carbonyl}amino)-1-piperidine-carboxylate D21 (300 mg) was added and the mixture heated at 80° C. for 2 h. The reaction mixture was cooled to room temperature, quenched with NH$_4$Cl (saturated solution) and extracted with ethyl acetate, Drying (MgSO$_4$), evaporation, and crystallisation from diethyl ether gave 150 mg of the title compound. M⁻–H=366.

Description 23

4,5-Difluoro-6-methyl-1-(4-piperidinyl)-1,3-dihydro-2H-benzimidazol-2-one hydrochloride (D23)

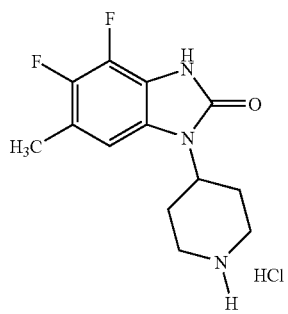

1,1-Dimethylethyl 4-(4,5-difluoro-6-methyl-2-oxo-2,3-dihydro-1H-benzimidazol-1-yl)-1-piperidinecarboxylate D22 (150 mg, 0.4 mmol) was dissolved in dichloromethane (5 ml) and treated with HCl in 1,4-dioxane (1 ml×4M) at room temperature for 4 h. Solvent was then evaporated to afford the title compound, 120 mg. M⁺+H=268.

Description 24

5-Bromo-1,3-difluoro-2-nitrobenzene (D24)

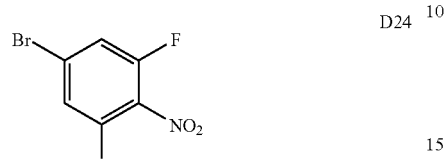

To a suspension of sodium perborate tetrahydrate (1.78 mmol, 0.27 g) in 10 ml of acetic acid stirred at 65° C. was added a solution of (4-bromo-2,6-difluorophenyl)amine (1.78 mmol, 0.42 g, 1 eq.) in 5 ml of acetic acid over one hour dropwise. The reaction was heated at 65° C. over 3 days. Sodium perborate tetrahydrate (2 eq., 3.56 mmol, 0.54 g) was added again. After 3 hours, sodium perborate tetrahydrate (1 eq., 1.78 mmol, 0.27 g) was added again. Additional sodium perborate tetrahydrate (3 eq., 5.34 mmol, 0.81 g) was again added. The reaction was then left overnight at 70° C. under reflux and under argon. The solution was then cooled to room temperature and poured onto ice and extracted with ethyl acetate (2×). The combined organics were washed with water and brine. The organics were dried over MgSO₄, filtered and the organic solvent was removed under reduced pressure to afford the crude product which was purified by silica chromatography (ethyl acetate-4% n-hexane 96%) to afford the title compound, 0.29 g, 68%.

¹H NMR δ (d⁶DMSO, 400 MHz): 7.964 (2H, d).

Description 25

5-Cyclopropyl-1,3-difluoro-2-nitrobenzene (D25)

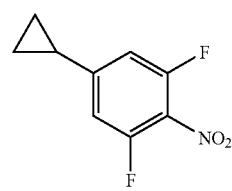

5-bromo-1,3-difluoro-2-nitrobenzene (D24, 560 mg, 2.35 mmol), cyclopropylboronic acid (1 eq., 2.35 mmol, 0.2 g), K₃PO₄ (3 eq., 7.1 mmol, 1.50 g), NaBr (1 eq., 2.35 mmol, 0.24 g) and Pd(PPh₃)₄ (280 mg) were added to 3 ml of dry toluene and the mixture was heated by microwave at 160° C. for 40 minutes. The mixture was then poured onto water (10 ml) and extracted with ethyl acetate (3×20 ml). The combined organics were dried over MgSO₄, filtered and the solvent was evaporated to afford 660 mg of brown crude product which was purified by silica gel chromatography (5-20% diethyl ether-40-60° petroleum ether) to afford the title compound as a yellow oil, 300 mg, 64%.

¹H NMR δ (d⁶DMSO, 400 MHz): 1.37 (2H, m), 1.60 (2H, m), 2.55 (1H, m), 7.71 (2H, d).

Description 26

1,1-Dimethylethyl 4-[(5-cyclopropyl-3-fluoro-2-nitrophenyl)amino]-1-piperidinecarboxylate (D26)

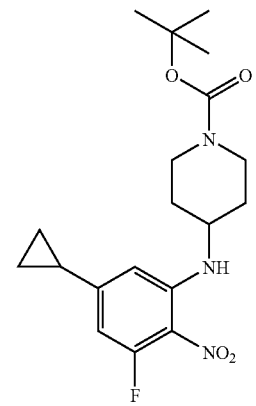

To a solution of 1,1-dimethylethyl 4-amino-1-piperidinecarboxylate (1 eq., 1.51 mmol, 302 mg) in dry dimethylformamide (10 ml), diisopropylethylamine (1 eq., 1.51 mmol, 0.26 ml) and 5-cyclopropyl-1,3-difluoro-2-nitrobenzene (D25, 1 eq., 1.51 mmol, 300 mg) were added at room temperature and the mixture was stirred under argon at 120° C. overnight. The crude mixture was then cooled to room temperature and poured onto water (10 ml). The aqueous solution was extracted with ethyl acetate (3×100 ml) and the organics were combined and washed with water and brine alternately (5×100 ml), dried over Na₂SO₄, filtered and the solvent was evaporated to afford the crude compound which was purified by chromatography (30% ethyl acetate-n-hexane 60%) to yield the title compound; 300 g, 0.79 mmol, 52%, M⁻–H=378.

Description 27

1,1-Dimethylethyl 4-[(2-amino-5-cyclopropyl-3-fluorophenyl)amino]-1-piperidinecarboxylate (D27)

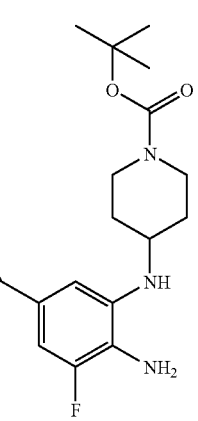

1,1-Dimethylethyl 4-[(5-cyclopropyl-3-fluoro-2-nitrophenyl)amino]-1-piperidinecarboxylate (D26, 0.8 mmol, 300 mg) was dissolved in MeOH (15 ml) and it was reduced by THALIS H-CUBE apparatus (bought from Asynt) using a palladium cartridge. The process yielded 280 mgs of the title compound, complete conversion, M+-COOC(CH3)3=250.

Description 28

1,1-Dimethylethyl 4-(6-cyclopropyl-4-fluoro-2-oxo-2,3-dihydro-1H-benzimidazol-1-yl)-1-piperidinecarboxylate (D28)

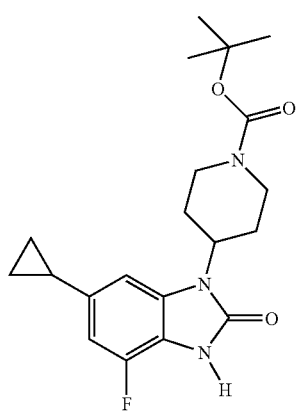

1,1-Dimethylethyl 4-[(2-amino-5-cyclopropyl-3-fluorophenyl)amino]-1-piperidine-carboxylate (D27, 0.80 mmol, 280 mg) was dissolved in 4 ml of tetrahydrofuran and CDI (1,1'-(oxomethanediyl)bis-1H-imidazole) (2.5 eq., 2.0 mmol, 0.33 g) at room temperature and the mixture was stirred at 50° C. for one overnight under argon. Extra CDI (1 eq., 0.13 g, 0.80 mmol) was added and the mixture was refluxed for two extra hours. The mixture was cooled to room temperature and the solvent was evaporated to afford the crude compound which was purified by chromatography (ethyl acetate (50)-n-hexane (50)) to yield the title compound, 102 mg, 36%, M−−H=374.

Description 29

6-Cyclopropyl-4-fluoro-1-(4-piperidinyl)-1,3-dihydro-2H-benzimidazol-2-one hydrochloride (D29)

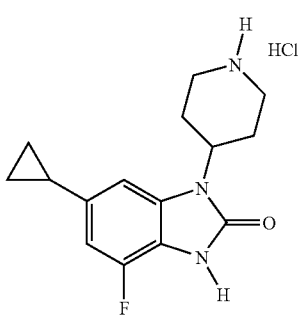

1,1-Dimethylethyl 4-(6-cyclopropyl-4-fluoro-2-oxo-2,3-dihydro-1H-benzimidazol-1-yl)-1-piperidinecarboxylate (D28, 0.28 mmol, 107 mg) was dissolved in 1 ml of dichloromethane and treated with HCl (1 ml of a 4M solution in 1,4-dioxane) at room temperature and the mixture stirred at room temperature for 3 hours. The solvent was evaporated to afford the title compound, 100 mg, 0.32 mmol, complete conversion, M++H=276.

Description 30

4,5-Difluoro-6-methyl-1-[1-(4-cyanotetrahydro-2H-pyran-4-yl)-4-piperidinyl]-1,3-dihydro-2H-benzimidazol-2-one (D30)

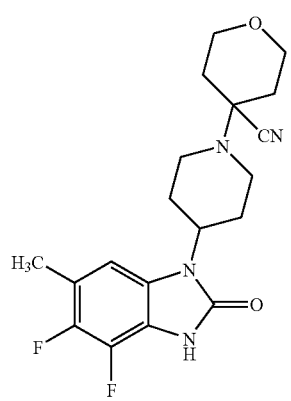

4,5-Difluoro-6-methyl-1-(4-piperidinyl)-1,3-dihydro-2H-benzimidazol-2-one hydrochloride (D23, 90 mg, 0.3 mmol) was converted to its free base using SCX, and this was then mixed with tetrahydro-4H-pyran-4-one (100 mg, 1.2 mmol), acetone cyanohydrin (100 mg, 1.2 mmol), magnesium sulfate (0.33 g) and dimethylacetamide (1 ml). The mixture was stirred under a slow stream of argon at 60° C. overnight, then partitioned between water and dichloromethane. Drying and evaporation gave the crystalline title compound from diethyl ether, 70 mg.

$^1$H NMR δ (DMSO, 400 MHz): 1.6-1.8 (4H, m), 2.1-2.4 (8H, m), 2.3 (3H, d), 3.2-3.5 (4H, m), 3.9 (1H, d), 4.2 (1H, m), 7.0 (1H, m).

Description 31

2-Bromo-6-fluoro-4-methylaniline (D31)

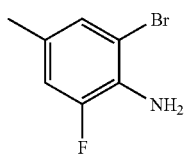

A stirred solution of 4-methyl-2-fluoroaniline (15 g, 0.12 mol) in acetic acid (120 ml) at 15° C. under argon was treated portionwise over 20 minutes with solid N-bromosuccinimide (24 g, 0.135 mol), then allowed to warm to room temperature and stirred for 1 hr. The reaction mixture was treated with water (500 ml) and extracted with ethyl acetate (2×300 ml). The combined extract was washed with water (2×500 ml), then excess 10% Na$_2$CO$_3$ solution (400 ml). The ethyl acetate solution was dried (Na$_2$SO$_4$) and concentrated under vacuum to leave the title compound as a dark red oil (24.0 g, 98%).

$^1$H NMR δ (CDCl$_3$, 400 MHz): 2.22 (3H, s), 3.95 (2H, br s), 6.78 (1H, d), 7.02 (1H, s).

Description 32

1,1-Dimethylethyl 4-({[(2-bromo-6-fluoro-4-methylphenyl)-amino]carbonyl}amino)-1-piperidinecarboxylate (D32)

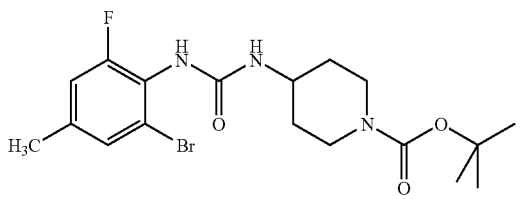

2-Bromo-6-fluoro-4-methylaniline (5.2 g, 25.5 mmol) (D31) was dissolved in 1,4-dioxane (40 ml) and bis(trichloromethyl)carbonate (9.3 mmol, 2.7 g) was added at room temperature and the mixture was heated to 60° C. for 15 minutes and it was then brought up to 100° C. for a further 15 minutes. The mixture was then cooled to room temperature, filtered and the solvent was thoroughly evaporated; the crude was redissolved in dichloromethane (40 ml) and 1,1-dimethylethyl 4-amino-1-piperidinecarboxylate (2 eq., 51 mmol, ~10.2 g) was added at room temperature very slowly. The mixture was stirred at room temperature for 1.5 hours, the solvent was then evaporated totally and the crude material was then left under vacuum for 10 minutes; dichloromethane was added again and the mixture obtained was filtered to afford the solid that is the first batch (5.2 g) of the desired product; the solvent was evaporated from the organic filtrate and the mixture obtained was re-dissolved into dichloromethane and filtered again to afford the second batch (1 g) of the desired product; the solvent was evaporated from the organic filtrate and the mixture obtained was re-dissolved into diethyl ether, filtered again, washed with methanol then with diethyl ether to afford the third batch (1.5 g) of the desired product. The three batches were combined to afford 7.7 g of the title compound, 70%, M$^+$+H=432.

EXAMPLES

Example 1a

4-Fluoro-6-methyl-1-[1-(tetrahydro-2H-pyran-4-yl)-4-piperidinyl]-1,3-dihydro-2H-benzimidazol-2-one hydrochloride (E1a)

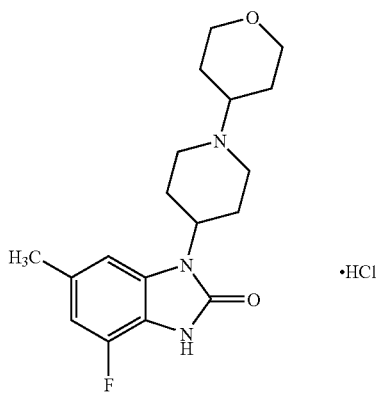

4-Fluoro-6-methyl-1-(4-piperidinyl)-1,3-dihydro-2H-benzimidazol-2-one hydrochloride (D5) (0.072 mmol, 21 mg) was dissolved in dichloromethane (2 ml) and triethylamine (3 eq., 0.216 mmol, 30 microliters), tetrahydro-4H-pyran-4-one (7 eq., 0.5 mmol, 47 microliters) were added and the mixture was stirred at room temperature for 10 minutes; sodium triacetoxyborohydride (7 eq., 0.5 mmol, 106 mg) was added at room temperature and the mixture was stirred at room temperature for one overnight. Reaction mixture was quenched with NaHCO$_3$ (saturated solution) and diluted with dichloromethane; the two phases were separated and the organic solvent was evaporated to afford the crude product. The crude obtained was dissolved in 1,2-dichloroethane (3 ml) and triethylamine (3 eq., 0.216 mmol, 30 microliters), tetrahydro-4H-pyran-4-one (7 eq., 0.5 mmol, 47 microliters) were added again and the mixture was stirred at room temperature for 10 minutes; sodium triacetoxyborohydride (7 eq., 0.5 mmol, 106 mg) was subsequently added at room temperature and the mixture was stirred at room temperature for 3 extra hours. Reaction mixture was quenched with NaHCO$_3$ (saturated solution) and diluted with dichloromethane; the two phases were separated and the organic solvent was evaporated to afford the crude product that was purified by chromatography (methanol-NH$_3$-dichloromethane) to afford 4-fluoro-6-methyl-1-[1-(tetrahydro-2H-pyran-4-yl)-4-piperidinyl]-1,3-dihydro-2H-benzimidazol-2-one, 10 mg, 42%, M$^+$+H=334, which was converted to the HCl salt using 1M HCl in diethyl ether.

$^1$H NMR (DMSO, 400 MHz, HCl salt) 1.74 (2H, m), 1.91 (2H, d), 2.03 (2H, d), 2.34 (3H, s), 2.80 (2H, q), 3.17 (3H, m), 3.34 (2H, m), 4.00 (2H, dd), 4.56 (1H, m), 6.75 (1H, d), 7.31 (1H, s), 10.5 (1H, s broad), 11.35 (1H, s broad); remaining $^1$H signals not discernible in spectrum

Example 1b

Scale-Up Procedure Using Alternative Process

4-Fluoro-6-methyl-1-[1-(tetrahydro-2H-pyran-4-yl)-4-piperidinyl]-1,3-dihydro-2H-benzimidazol-2-one Free Base (E1b)

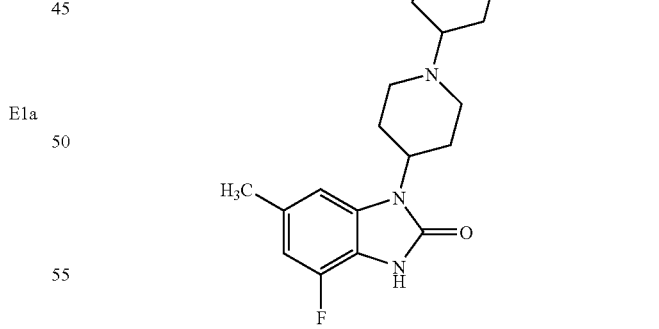

4-Fluoro-6-methyl-1-(4-piperidinyl)-1,3-dihydro-2H-benzimidazol-2-one (12.5 mmol, 3.6 g) (D5a) was dissolved in dichloromethane (50 ml), diisopropylethylamine (3 eq., 37.6 mmol, ~6.4 ml), and tetrahydro-4H-pyran-4-one (4 eq., 50 mmol, ~5 g) were added in that order at room temperature; sodium triacetoxyborohydride (3 eq., 37.6 mmol, ~8 g) was added at room temperature and the mixture was stirred at room temperature for one overnight. The reaction mixture was diluted with dichloromethane (100 ml) and quenched with NaHCO$_3$ (saturated aqueous solution); methanol was added to dissolve the solid which developed in the organic layer; the two phases were separated and the aqueous phase was extracted with dichloromethane (2×); the combined organics were washed with brine, dried over Na$_2$SO$_4$, filtered and the solvent was evaporated to afford 3.8 g, 92%. The material was triturated with diethyl ether and filtered to afford 3.6 g title compound. This was dissolved in MeOH/DCM and 2 eq of HCl (1M in Et$_2$O) were added. The mixture was stirred at room temperature for 10 minutes, solvent was evaporated and the solid was triturated with Et$_2$O to afford another batch, 3.8 g, pale grey solid.

$^1$H NMR □ (DMSO, 600 MHz, free base) 1.45 (2H, m), 1.70 (4H, m), 2.25 (4H, m), 2.33 (3H, s), 2.48 (1H, m), 3.01 (2H, m), 3.33 (2H, t), 3.88 (2H, m), 4.12 (1H, m), 6.65 (1H, d), 6.88 (1H, s), and 11.3 (1H, bs).

Example 1c

Scale-Up Procedure

4-Fluoro-6-methyl-1-[1-(tetrahydro-2H-pyran-4-yl)-4-piperidinyl]-1,3-dihydro-2H-benzimidazol-2-one hydrochloride (E1c)

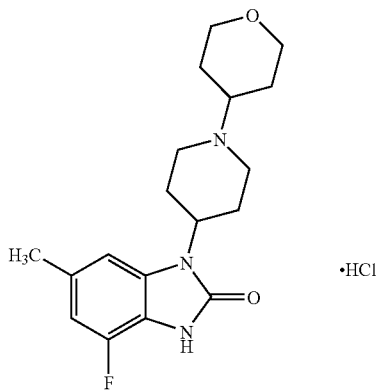

4-Fluoro-6-methyl-1-[1-(tetrahydro-2H-pyran-4-yl)-4-piperidinyl]-1,3-dihydro-2H-benzimidazol-2-one free base (102.73 mmol, 34.25 g, 1 wt) was suspended in methanol (10 vol. 342 ml). HCl 1M in diethyl ether (154 ml, 1.5 eq.) was added dropwise in 20 min. The slurry was magnetically stirred at ambient temp. for 3 hours. The solvents were evaporated and the solid triturated in diethyl ether (14.5 vol., 500 ml) for 20 min. Diethyl ether was decanted and the white solid was dried under high vacuum at 40° C. overnight. Residual MeOH (7% w/w by NMR) was found. The solid was dried under high vacuum overnight at 40° C. The solid was triturated in diethyl ether (14.5 vol, 500 ml), filtered and dried again in the oven at 40° C./high vacuum for 4 hours, then at 60° C. overnight then at 80° C. for two hours. 36.1 g, 95%.

$^1$H NMR □ (DMSO, 600 MHz, hydrochloride) 1.69 (2H, m), 1.89 (4H, m), 1.95 (2H, m), 2.31 (3H, s), 2.67 (2H, m), 3.17 (2H, m), 3.34 (2H, m), 3.42 (1H, m), 3.57 (2H, m), 3.98 (2H, m), 4.52 (1H, m), 6.75 (1H, d), 7.15 (1H, bs), 9.95 (1H, m), and 11.36 (1H, s).

Example 1d

4-Fluoro-6-methyl-1-[1-(tetrahydro-2H-pyran-4-yl)-4-piperidinyl]-1,3-dihydro-2H-benzimidazol-2-one monocitrate (E1d)

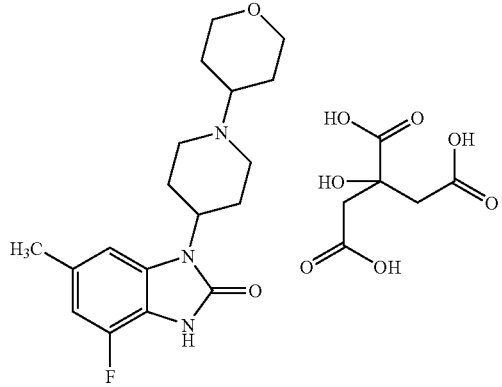

4-Fluoro-6-methyl-1-[1-(tetrahydro-2H-pyran-4-yl)-4-piperidinyl]-1,3-dihydro-2H-benzimidazol-2-one free base (1.499 mmol, 500 mg, 1 wt) was weighed into a 250 ml round bottomed flask, citric acid (1 eq, 1.499 mmol, 288 mg,) was added. Acetonitrile (95 vol. 47.5 ml) was added and a white slurry obtained, dissolution was not achieved with heating using a hot air gun. The slurry was magnetically stirred at 35° C. for four days under nitrogen. The solid was cooled and isolated by vacuum filtration and washed with acetonitrile (10 vol. 5 ml). The solid (1.0 g not dried) was recombined with the mother liquors plus acetonitrile (29 vol., 14.5 ml) and n-propanol (22 vol. 11 ml) was added. The slurry was stirred at ambient temperature overnight. The solid was isolated by vacuum filtration and washed with acetonitrile (10 vol, 5 ml). The white solid was dried under vacuum at 60° C. for 25 hours. 506 mg, 64%.

$^1$H NMR □ (DMSO, 400 MHz, citrate) 1.60 (2H, m), 1.86 (4H, m), 2.36 (3H, s), 2.50 (2H, m), 2.56 (2H, d), 2.64 (2H, d), 2.79 (2H, m), 3.04 (1H, m), 3.32 (4H, m), 3.98 (2H, dd), 4.33 (1H, t), 6.75 (1H, d), 6.93 (1H, m), 11.27 (3H, m), and 11.29 (1H, s)

Example 1e

4-Fluoro-6-methyl-1-[1-(tetrahydro-2H-pyran-4-yl)-4-piperidinyl]-1,3-dihydro-2H-benzimidazol-2-one methanesulfonate (E1e)

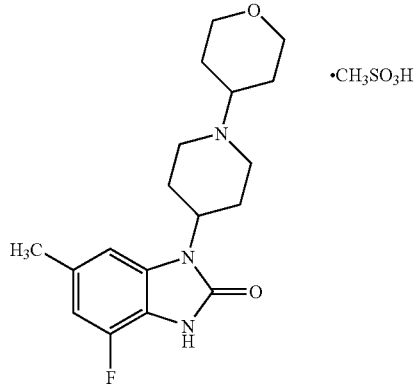

4-Fluoro-6-methyl-1-[1-(tetrahydro-2H-pyran-4-yl)-4-piperidinyl]-1,3-dihydro-2H-benzimidazol-2-one free base (1.499 mmol, 500 mg, 1 wt) was weighed into a 250 ml round bottomed flask, acetonitrile (95 vol., 47.5 ml) and n-propanol (80 vol., 40 ml) were added, giving a white slurry. Methanesulfonic acid (1 eq, 1.499 mmol, 97 □l) was pipetted into the flask. The contents of the flask were heated using a hot air gun—the slurry dissolved and a white precipitate formed. The precipitate was magnetically stirred at 35° C. for four days under nitrogen. After cooling to ambient temperature, the solid was isolated by vacuum filtration and washed with acetonitrile (10 vol. 5 ml). The white solid was dried under high vacuum at 60° C. for 25 hours. 561 mg, 87%, white solid.

$^1$H NMR □ (DMSO, 500 MHz, methanesulfonate salt) 1.69 (2H, m), 1.96 (4H, m), 2.31 (3H, s), 2.34 (3H, s), 2.64 (2H, m), 3.17 (2H, m), 3.34 (2H, m), 3.48 (1H, m), 3.62 (2H, d), 3.98 (2H, d), 4.52 (1H, m), 6.75 (1H, d), 6.96 (1H, bs), 9.25 (1H, m), and 11.36 (1H, s).

Example 1f

Alternative Method for 4-fluoro-6-methyl-1-[1-(tetrahydro-2H-pyran-4-yl)-4-piperidinyl]-1,3-dihydro-2H-benzimidazol-2-one Stage 1 Preparation of 1,1-dimethylethyl (3,5-difluoro-4-nitrophenyl)acetate

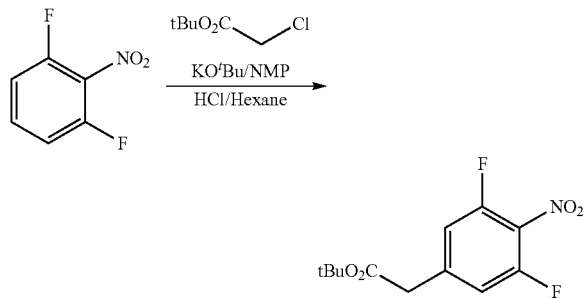

A mixture of potassium tert-butoxide (248 g) in NMP (2000 ml) was cooled under nitrogen to −20° C. A mixture of 2,6-difluoronitrobenzene (10 g) and tert-butylchloroacetate (160 g) in NMP (2000 ml) was added slowly at −10° C. to −20° C. over 1.5 hours. After 30 minutes, a further portion of potassium tert-butoxide (88 g) was added. The reaction mass was quenched into 1600 ml of 2M HCl and 1 kg crushed ice, then 2000 ml hexane was added and the mixture stirred for 10 minutes. The layers were separated and the aqueous layer was extracted with hexane (2×1500 ml). The combined hexane layers were washed with saturated brine (2×1000 ml), then dried over anhydrous sodium sulphate, then filtered and washed with 200 ml hexane. The solution was then evaporated to give the title compound as a brown liquid (152 g).

Stage 2 Preparation of (3,5-difluoro-4-nitrophenyl)acetic acid

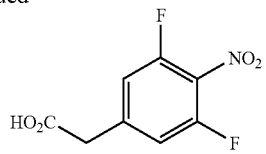

1,1-dimethylethyl (3,5-difluoro-4-nitrophenyl)acetate (150 g) and 4M HCl in 1,4-dioxane (1150 ml) was stirred for 18 h at about 25° C. Nitrogen was bubbled through the mixture to remove excess HCl over 7 hours, then the mixture was concentrated. Toluene (300 ml) was distilled off then the residue was stirred with hexane (300 ml) for 10 minutes. The hexane was decanted off, and the residue stirred with hexane (150 ml) for 10 minutes, then the hexane was decanted off. The residue was stirred with toluene (450 ml) for 2 hours at around 25° C. The solid was filtered and washed with 1:1 toluene/hexane (300 ml), then dried under vacuum to give the title compound as a brown fine powder (41.5 g).

300 MHz NMR in DMSO-d$_6$. DMSO-d$_5$ as reference at 2.5 ppm.

δ(ppm): 3.78 (2H) s; 7.44 (2H) d;

Stage 3 Preparation of 1,3-difluoro-5-methyl-2-nitrobenzene

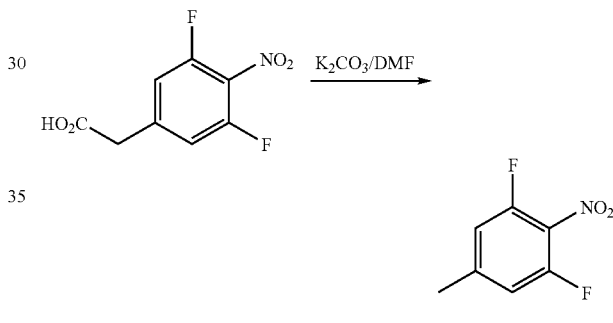

A mixture of (3,5-difluoro-4-nitrophenyl)acetic acid (41 g), potassium carbonate (24.6 g) and DMF (205 ml) was slowly heated to about 50° C. for 30 minutes. The reaction was then cooled to about 25° C. and quenched into 2M HCl (1025 ml) and hexane (400 ml) and stirred for 10 minutes. The layers were separated and the aqueous layer was extracted with hexane (400 ml). The combined hexane layers were washed with saturated brine (2×200 ml), then dried with anhydrous sodium sulphate, then the solution was concentrated to give the title compound as a low melting solid (26 g).

300 MHz NMR in CDCl$_3$. TMS as reference at 0.0 ppm.

δ(ppm): 2.44 (3H) s; 6.91 (2H) d

Stage 4 Preparation of 1-(tetrahydro-2H-pyran-4-yl)-4-piperidinamine, dihydrochloride

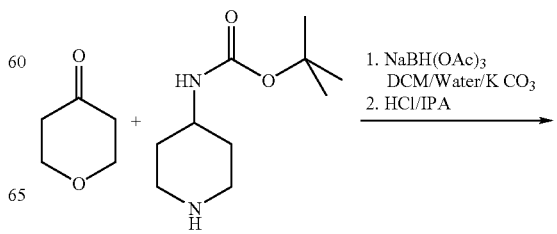

-continued

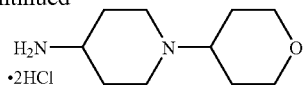

To a solution of 1,1-dimethylethyl 4-piperidinylcarbamate (50 g) was added tetrahydro-4H-pyran-4-one (35.75 g) in dry DCM (1000 ml), then was added sodium triacetoxyborohydride (141 g) portion wise over 10 minutes at about 25° C. The mixture was stirred under nitrogen for about 30 hours, then cooled to 0° C. Water (107 ml) was added portion wise in 20 minutes, followed by saturated aqueous potassium carbonate (178 ml) and saturated brine (178 g in 178 ml). The mixture was stirred for 10 minutes at about 25° C., then the layers were separated and the organic layer washed with saturated brine (3×214 ml). After drying over anhydrous sodium sulphate, the organic layer was concentrated and the residue was treated with 100 ml isopropanol and reconcentrated. The residue was slowly heated to reflux with 11% HCl in isopropanol (200 ml) for 2 hours then cooled to about 25° C. The solid was filtered, and slurry washed with diethyl ether (100 ml), then dried under high vacuum to give the title product (43 g).

300 MHz NMR in $D_2O$. HDO signal as reference at 4.70 ppm.

δ(ppm): 1.72 (2H) m; 1.88 (2H) m; 1.99 (2H) m; 2.29 (2H) m; 3.08 (2H) m; 3.40 (4H) m; 3.65 (2H) m; 4.02 (2H) m Stage 5 Preparation of N-(3-fluoro-5-methyl-2-nitrophenyl)-1-(tetrahydro-2H-pyran-4-yl)-4-piperidinamine

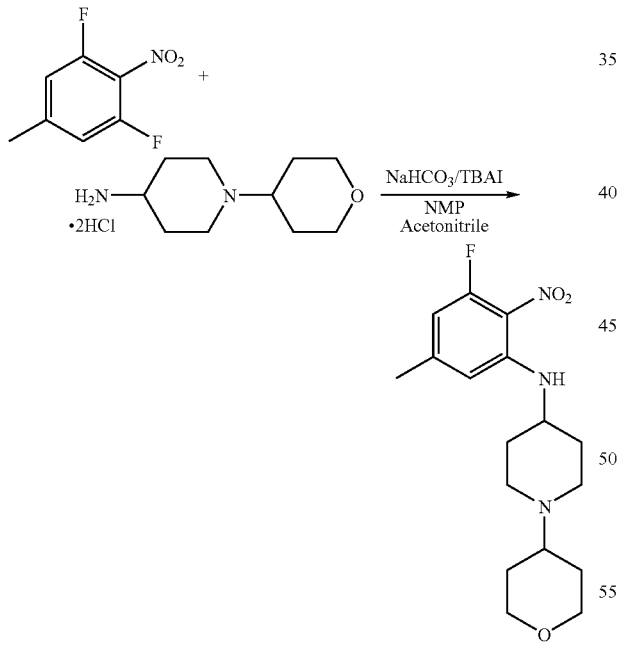

A mixture of 1,3-difluoro-5-methyl-2-nitrobenzene (1 g), 1-(tetrahydro-2H-pyran-4-yl)-4-piperidinamine, dihydrochloride (1.63 g), sodium bicarbonate (1.94 g) and tetrabutyl ammonium iodide (100 mg) in NMP (15 ml) was slowly heated at about 50° C. for 3 hours. After cooling to about 25° C., the reaction mixture was added to ethyl acetate (15 ml) and saturated brine (15 ml). The layers were separated and the aqueous extracted with ethyl acetate (15 ml). The combined ethyl acetate layers were then washed with saturated brine (4×4 ml), dried with 2 g anhydrous sodium sulphate then concentrated under vacuum. The residue was heated with acetonitrile (4 ml) to about 60° C. to give a solution, then cooled to 0 to 5° C. and stirred for 1 hour. The solid was filtered, washed with chilled acetonitrile (2 ml), then dried at 40-45° C. under high vacuum to give the title compound as an orange solid (0.83 g).

300 MHz NMR in $CDCl_3$. TMS as reference at 0.0 ppm.

δ(ppm): 1.62 (4H) m; 1.76 (2H) m; 2.05 (2H) m; 2.30 (3H) s; 2.42 (2H) m; 2.51 (1H) m; 2.88 (2H) m; 3.390 (2H) m; 3.49 (1H) m; 4.05 (2H) m; 6.23 (1H) d; 6.36 (1H) s; 7.51 (1H) m;

Stage 6 Preparation of (2-amino-3-fluoro-5-methylphenyl)[1-(tetrahydro-2H-pyran-4-yl)-4-piperidinyl]amine

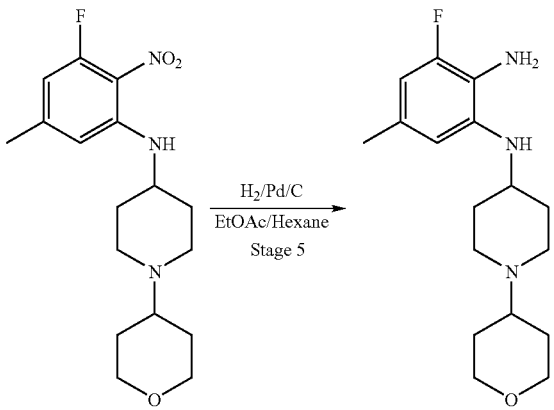 [SMILES: Cc1cc(F)c([N+](=O)[O-])c(NC2CCN(C3CCOCC3)CC2)c1 ; Cc1cc(F)c(N)c(NC2CCN(C3CCOCC3)CC2)c1]

A mixture of N-(3-fluoro-5-methyl-2-nitrophenyl)-1-(tetrahydro-2H-pyran-4-yl)-4-piperidinamine (10 g), ethyl acetate (200 ml) and 10% Pd/C (1 g), was stirred at about 30° C. under hydrogen pressure for 9 hours. The catalyst was filtered and the filtrate concentrated. The residue was stirred with ethyl acetate (20 ml) and hexane (40 ml) for 1 hour at room temperature then filtered and the solid dried at 50° C. to give the title compound as a solid (6.3 g).

300 MHz NMR in $CDCl_3$. TMS as reference at 0.0 ppm.

δ(ppm): 1.50 (2H) m; 1.64 (2H) m; 1.76 (2H) m; 2.08 (2H) m; 2.23 (3H) s; 2.34 (2H) m; 2.50 (1H) m; 2.94 (2H) m; 3.07 (2H) br s; 3.27 (1H) m; 3.38 (2H) m; 4.02 (2H) m; 6.23 (1H) s; 6.32 (1H) d;

Stage 7 Preparation of 4-fluoro-6-methyl-1-[1-(tetrahydro-2H-pyran-4-yl)-4-piperidinyl]-1,3-dihydro-2H-benzimidazol-2-one

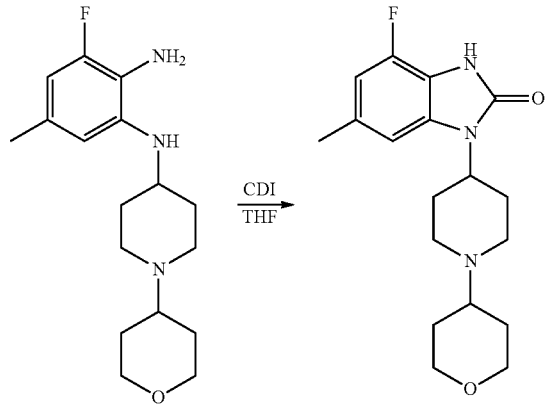

A mixture of (2-amino-3-fluoro-5-methylphenyl)[1-(tetrahydro-2H-pyran-4-yl)-4-piperidinyl]amine (0.5 g), N,N'-carbonyldiimidazole (0.66 g) and tetrahydrofuran (7 ml) was heated to reflux. After 30 minutes, tetrahydrofuran (3 ml) was added, and the mixture heated at reflux for a further 1½ hours. The reaction mixture was filtered and washed with tetrahydrofuran (10 ml), then the solid was dried at 40-45° C. under high vacuum to give the title compound (0.323 g).

300 MHz NMR in $CDCl_3$+TFA+1 drop DMSO-$d_6$. TMS as reference at 0.0 ppm.

δ(ppm): 2.00 (2H) m; 2.12 (2H) m; 2.22 (2H) m; 2.37 (3H) s; 2.92 (2H) m; 3.24 (2H) m; 3.60 (3H) m; 3.87 (2H) m; 4.29 (2H) m; 4.63 (1H) m; 6.81 (1H) d; 6.84 (1H) s;

Example 2

6-Chloro-4-fluoro-1-[1-(tetrahydro-2H-pyran-4-yl)-4-piperidinyl]-1,3-dihydro-2H-benzimidazol-2-one hydrochloride (E2)

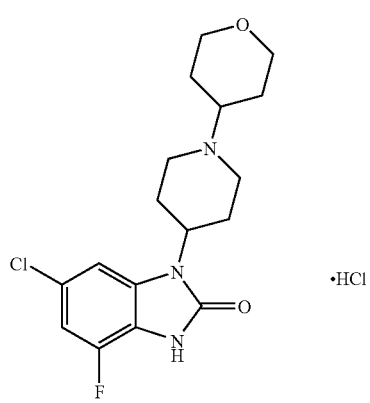

E2

6-Chloro-4-fluoro-1-(4-piperidinyl)-1,3-dihydro-2H-benzimidazol-2-one hydrochloride D9 (0.36 mmol, 0.1 g) was dissolved in dichloromethane (10 ml) and triethylamine (3 eq., 1.08 mmol, 80 microliters), tetrahydro-4H-pyran-4-one (4.5 eq., 1.62 mmol, 162 mg), sodium triacetoxyborohydride (4.5 eq., 1.62 mmol, 345 mg) were added at room temperature and the mixture was stirred at room temperature for 2 hours. Additional tetrahydro-4H-pyran-4-one (2 eq., 0.72 mmol, 72 microliters) and sodium triacetoxyborohydride (2 eq., 0.72 mmol, 0.015 g) were added at room temperature and the mixture was stirred at room temperature for two further hours. The mixture was quenched with water and brought to pH 10 by sodium hydroxide (aqueous solution). The organic phase was separated from the aqueous phase (by hydrophobic filters) and the organic solvent was evaporated to afford the crude product that was purified by chromatography (methanol-$NH_3$-dichloromethane) to afford 6-chloro-4-fluoro-1-[1-(tetrahydro-2H-pyran-4-yl)-4-piperidinyl]-1,3-dihydro-2H-benzimidazol-2-one, 15 mg, 11%, $M^++H$=354 and 356, which was converted to the hydrochloride salt using 1M HCl in diethyl ether.

$^1$H NMR (free base) □ (DMSO, 400 MHz) 1.45 (2H, m), 1.68 (4H, t), 2.29 (4H, m), 3.00 (2H, d), 3.27 (2H, t), 3.89 (2H, dd), 4.10 (1H, m broad), 7.08 (1H, d), 7.20 (1H, s), 11.6 (1H, s broad); remaining $^1$H signals not discernible in spectrum.

Example 3

4-Fluoro-6-methoxy-1-[1-(tetrahydro-2H-pyran-4-yl)-4-piperidinyl]-1,3-dihydro-2H-benzimidazol-2-one hydrochloride (E3)

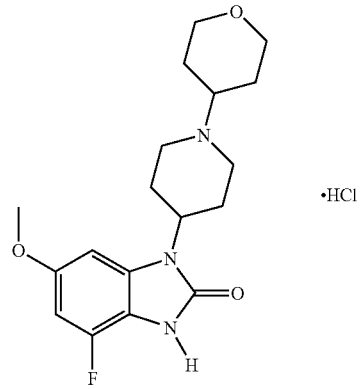

E3

4-Fluoro-6-methoxy-5-1-(4-piperidinyl)-1,3-dihydro-2H-benzimidazol-2-one hydrochloride D14 (100 mg, 0.33 mmol), Ti(iPrO)$_4$ (0.3 ml, 1.0 mmol), and tetrahydro-4H-pyran-4-one (100 mg, 1.0 mmol, 0.3 ml) were stirred together at room temperature for 1 h; dry methanol (2 ml) followed by NaBH$_3$CN (60 mg, 1 mmol) were added and the mixture was stirred at room temperature for 4 h. The crude mixture was then quenched with methanol and it was purified first by SCX column chromatography followed by silica gel chromatography (methanol-NH$_3$-dichloromethane). Conversion to the hydrochloride gave the title compound, 30 mg, MH$^+$=350, $^1$H NMR (HCl salt). (DMSO-$d_6$) □: 1.75 (2H, m), 1.92 (2H, m), 2.08 (2H, m), 2.81 (2H, m), 3.20 (2H, m), 3.36 (2H, m), 3.44 (1H, m), 3.82 (3H, s) 4.01 (2H, m), 4.62 (1H, m), 6.59 (1H, d, J=12 Hz), 7.61 (1H, s), 10.82 (1H, bs) and 11.40 (1H, s); remaining $^1$H signals not discernible in spectrum Example 4

4,5-Difluoro-6-methyl-1-[1-(tetrahydro-2H-pyran-4-yl)-4-piperidinyl]-1,3-dihydro-2H-benzimidazol-2-one hydrochloride (E4)

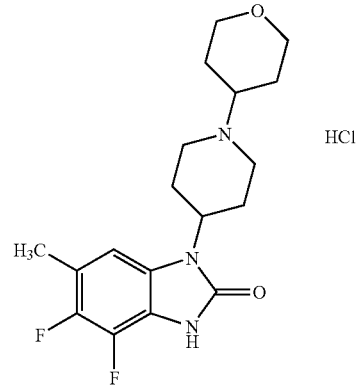

E4

4,5-Difluoro-6-methyl-1-(4-piperidinyl)-1,3-dihydro-2H-benzimidazol-2-one hydrochloride D23 (120 mg) was dissolved in dichloromethane (5 ml) and diisopropylethylamine (0.2 ml, 1.2 mmol), tetrahydro-4H-pyran-4-one (0.2 ml, 2.0 mmol) and sodium triacetoxyborohydride (250 mg, 1.2 mmol) were added and the mixture stirred at room temperature for 4 h. The mixture was partitioned with water/MDC at pH9. Drying (MgSO₄), evaporation, and crystallisation of the residue from diethyl ether, washing with dichloromethane gave the title compound free base, which was converted to the hydrochloride. Trituration with diethyl ether gave 35 mg of hydrochloride salt. MH⁺=352, ¹H NMR(HCl salt) (DMSO) □□ 1.7 (2H, m), 2.0 (4H, m), 2.3 (3H, d, J=2 Hz), 2.8 (2H, m), 3.1 (3H, m), 4.0 (2H, bd), 4.5 (1H, m), 7.3 (1H, d, J=5 Hz), 10.3 (1H, bs), and 11.1 (1H, bs); remaining ¹H signals not discernible in spectrum Example 5

6-Cyclopropyl-4-fluoro-1-[1-(tetrahydro-2H-pyran-4-yl)-4-piperidinyl]-1,3-dihydro-2H-benzimidazol-2-one hydrochloride (E5)

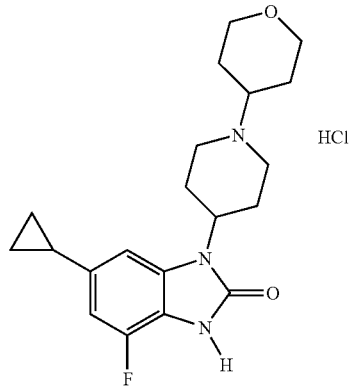

6-Cyclopropyl-4-fluoro-1-(4-piperidinyl)-1,3-dihydro-2H-benzimidazol-2-one hydrochloride (D29, 0.28 mmol, 86 mg), was dissolved in 1,2-dichloroethane (3 ml) and triethylamine (3 eq., 0.83 mmol, 0.086 g), tetrahydro-4H-pyran-4-one (7 eq., 1.99 mmol, 0.2 g) and sodium triacetoxyborohydride (3 eq., 0.83 mmol, 0.052 g) were added at room temperature and the mixture was stirred at room temperature for one overnight. The reaction mixture was quenched with NaHCO₃ (saturated solution) and diluted with dichloromethane, then the two phases were separated by hydrophobic filter and the aqueous was washed with dichloromethane again. The organic phases were combined and the solvent was evaporated to afford the crude product which was purified by chromatography (methanol-NH₃-dichloromethane) to afford the free base of the title compound, 100 mg, 98%, M⁺+H=360. This material was dissolved in methanol (2 ml) and HCl (3 eq., 0.046 ml from a 1M solution in diethyl ether) was added at room temperature and the mixture was stirred at room temperature for 5 minutes. The solvent was subsequently evaporated to afford the title compound, 90 mg, 82%.

¹H NMR δ (d⁶DMSO, 400 MHz, monohydrochloride): 0.75 (2H, m), 0.91 (2H, m), 1.76 (2H, m), 1.93 (2H, m), 2.04 (2H, d), 2.84 (2H, q), 3.18 (4H, q), 3.44 (1H, m), 3.59 (2H, d), 3.99 (2H, m), 4.11 (1H, m broad), 4.57 (1H, m), 6.63 (1H, d), 7.19 (1H, s), 10.85 (1H, s broad), 11.30 (1H, s).

Example 6

4,5-Difluoro-6-methyl-1-[1-(4-methyltetrahydro-2H-pyran-4-yl)-4-piperidinyl]-1,3-dihydro-2H-benzimidazol-2-one hydrochloride (E6)

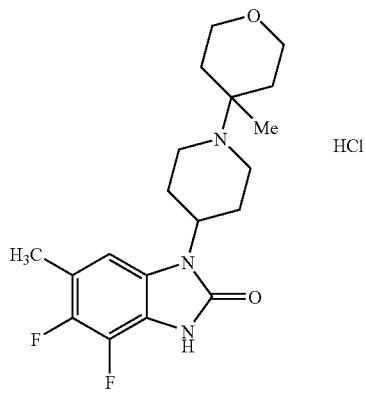

A stirred solution of 3M methylmagnesium bromide in diethyl ether (0.7 ml, 2.0 mmol), was treated with a tetrahydrofuran (5 ml) solution of 4,5-difluoro-6-methyl-1-[1-(4-cyanotetrahydro-2H-pyran-4-yl)-4-piperidinyl]-1,3-dihydro-2H-benzimidazol-2-one (D30, 70 mg, 6.2 mmol) for 2 h at room temperature, then poured into a saturated aqueous solution of Rochelle salt and extracted with dichloromethane. The organic layer was dried (MgSO₄) evaporated and purified by chromatography (10 g silica, 0-10% methanol in dichloromethane with 0.2M ammonia) to give the title compound (35 mg), isolated as the hydrochloride salt from diethyl ether. MH⁺=366.

¹H NMR (HCl salt) δ (d⁶DMSO): 1.4 (3H, s), 1.9 (4H, m), 2.1 (2H, m), 2.3 (3H, d, J=2 Hz), 2.8 (2H, m) 3.2 (2H, m), 3.9 (2H, m), 4.6 (1H, m), 7.5 (1H, d, J=5 Hz), 10.3 (1H, bs), and 11.6 (1H, s); remaining protons not discernible from spectrum.

All 1H NMR are consistent with the structures shown.

All publications, including but not limited to patents and patent applications, cited in this specification are herein incorporated by reference as if each individual publication were specifically and individually indicated to be incorporated by reference herein as though fully set forth.

The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims.

The invention claimed is:

1. 4-Fluoro-6-methyl-1-[1-(tetrahydro-2H-pyran-4-yl)-4-piperidinyl]-1,3-dihydro-2H-benzimidazol-2-one or a pharmaceutically acceptable salt thereof.

2. A compound of claim 1 chosen from:
   4-Fluoro-6-methyl-1-[1-(tetrahydro-2H-pyran-4-yl)-4-piperidinyl]-1,3-dihydro-2H-benzimidazol-2-one hydrochloride;
   4-Fluoro-6-methyl-1-[1-(tetrahydro-2H-pyran-4-yl)-4-piperidinyl]-1,3-dihydro-2H-benzimidazol-2-one monocitrate; or 4-Fluoro-6-methyl-1-[1-(tetrahydro-2H-pyran-4-yl)-4-piperidinyl]-1,3-dihydro-2H-benzimidazol-2-one methanesulfonate.

3. A pharmaceutical composition comprising an effective amount of a compound of claim 1 and a pharmaceutically acceptable carrier thereof.

4. A pharmaceutical composition comprising an effective amount of a compound of claim 2 and a pharmaceutically acceptable carrier thereof.

5. A method of treating a psychotic disorder or cognitive impairment, which comprises administering to a mammal in need thereof an effective amount of a compound of claim 1.

6. A method of treating schizophrenia, which comprises administering to a mammal in need thereof an effective amount of a compound of claim 1.

7. A method of treating cognitive impairment which comprises administering to a mammal in need thereof an effective amount of a compound of claim 1.

* * * * *